US007276608B2

(12) United States Patent
Sher et al.

(10) Patent No.: US 7,276,608 B2
(45) Date of Patent: Oct. 2, 2007

(54) TETRAHYDROQUINOLINE DERIVATIVES AS CANNABINOID RECEPTOR MODULATORS

(75) Inventors: Philip M. Sher, Plainsboro, NJ (US); Chongqing Sun, East Windsor, NJ (US); Richard B. Sulsky, West Trenton, NJ (US); Gang Wu, Princeton, NJ (US); William R. Ewing, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 450 days.

(21) Appl. No.: 10/889,268

(22) Filed: Jul. 12, 2004

(65) Prior Publication Data
US 2005/0009870 A1   Jan. 13, 2005

Related U.S. Application Data

(60) Provisional application No. 60/486,774, filed on Jul. 11, 2003.

(51) Int. Cl.
C07D 215/38   (2006.01)

(52) U.S. Cl. ...................... 546/156; 546/157

(58) Field of Classification Search ................ 546/156, 546/157
See application file for complete search history.

(56) References Cited

U.S. PATENT DOCUMENTS

| 4,371,720 | A | 2/1983 | Johnson et al. |
| 5,013,387 | A | 5/1991 | Goodwin et al. |
| 5,081,122 | A | 1/1992 | Ward |
| 5,292,736 | A | 3/1994 | Kumar et al. |
| 5,403,857 | A | 4/1995 | Edwards et al. |
| 5,773,203 | A | 6/1998 | Kimura et al. |
| 5,891,909 | A | 4/1999 | Soll et al. |
| 5,972,961 | A * | 10/1999 | Hewawasam et al. ...... 514/312 |
| 6,107,252 | A | 8/2000 | Andree et al. |
| 6,541,661 | B1 | 4/2003 | Delorme et al. |
| 6,559,144 | B2 | 5/2003 | Diefenbach et al. |
| 2001/0021709 | A1 | 9/2001 | Diefenbach et al. |
| 2003/0232804 | A1 | 12/2003 | Pinto et al. |
| 2004/0002495 | A1 | 1/2004 | Sher et al. |
| 2004/0082798 | A1 | 4/2004 | Alonso-Alija et al. |

FOREIGN PATENT DOCUMENTS

| EP | 044451 | 9/1991 |
| EP | 0570920 | 11/1993 |
| EP | 1340500 | 9/2003 |
| FR | 2735774 | 12/1996 |
| GB | 2272439 | 5/1984 |
| WO | WO94/12466 | 6/1994 |
| WO | WO96/36596 | 11/1996 |
| WO | WO97/29079 | 8/1997 |
| WO | WO98/41519 | 9/1998 |
| WO | WO99/02499 | 1/1999 |
| WO | WO 00/13508 | 3/2000 |
| WO | WO 01/79261 | 10/2001 |
| WO | WO 02/30357 | 4/2002 |
| WO | WO 02/070510 | 9/2002 |
| WO | WO 03/007887 | 1/2003 |
| WO | WO 03/020217 | 3/2003 |
| WO | WO 03/027069 | 4/2003 |
| WO | WO 03/027076 | 4/2003 |
| WO | WO 03/027114 | 4/2003 |
| WO | WO 03/035005 | 5/2003 |
| WO | WO 03/051850 | 6/2003 |
| WO | WO 03/051851 | 6/2003 |
| WO | WO 03/103677 | 12/2003 |
| WO | WO 2004/015130 | 2/2004 |

OTHER PUBLICATIONS

Hewawasam, Bioorganic & Medicinal Chemistry Letters, vol. 12 (2002), pp. 1779-1783.*
U.S. Appl. No. 10/889,274, filed Jul. 12, 2004, Sun et al.

* cited by examiner

Primary Examiner—D. Margaret Seaman
(74) Attorney, Agent, or Firm—Maureen S. Gibbons; Sammy G. Duncan, Jr.

(57) ABSTRACT

The invention provides for compounds of formula I

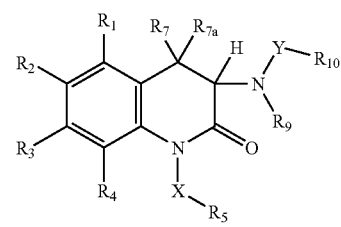

wherein the substitutents are as described herein.

Further provided are methods of using such compounds for the treatment of eating disorders, metabolic disorders, obesity, cognitive disorders, neurological disorders, pain disorders, inflammation disorders, in the promotion of smoking cessation and for the treatment of other psychiatric disorders Also provided are pharmaceutical compositions containing such compounds and pharmaceutical combinations of the compounds of the invention with other therapeutic agents.

4 Claims, No Drawings

TETRAHYDROQUINOLINE DERIVATIVES AS CANNABINOID RECEPTOR MODULATORS

RELATED APPLICATIONS

This application claims priority benefit under Title 35 § 119(e) of U.S. provisional Application No. 60/486,774, filed Jul. 11, 2003, the contents of which are herein incorporated by reference.

FIELD OF THE INVENTION

The present invention relates to tetrahydroquinoline containing compounds and compositions, to processes for preparing such compounds and compositions, and to the use of such compounds and compositions in the treatment of eating disorders, metabolic disorders, obesity, cognitive disorders, neurological disorders, pain disorders, inflammation disorders, in the promotion of smoking cessation and for the treatment of other psychiatric disorders.

BACKGROUND OF THE INVENTION

Delta-9-tetrahydrocannabinol or Delta-9 THC, the principle active component of Cannabis sativa (marijuana), is a member of a large family of lipophilic compounds (i.e., cannabinoids) that mediate physiological and psychotropic effects including regulation of appetite, immunosuppression, analgesia, inflammation, emesis, anti-nocioception, sedation, and intraocular pressure. Other members of the cannabinoid family include the endogenous (arachidonic acid-derived) ligands, anandamide, 2-arachidonyl glycerol, and 2-arachidonyl glycerol ether. Cannabinoids work through selective binding to and activation of G-protein coupled cannabinoid receptors. Two types of cannabinoid receptors have been cloned including CB-1 (L. A. Matsuda, et al., *Nature*, 346, 561-564 (1990)), and CB-2 (S. Munro, et al., *Nature*, 365, 61-65 (1993)). The CB-1 receptor is highly expressed in the central and peripheral nervous systems (M. Glass, et al., *Neuroscience*, 77, 299-318 (1997)), while the CB-2 receptor is highly expressed in immune tissue, particularly in spleen and tonsils. The CB-2 receptor is also expressed on other immune system cells, such as lymphoid cells (S. Galiegue, et al., *Eur J Biochem*, 232, 54-61 (1995)). Agonist activation of cannabinoid receptors results in inhibition of cAMP accumulation, stimulation of MAP kinase activity, and closure of calcium channels.

There exists substantial evidence that cannabinoids regulate appetitive behavior. Stimulation of CB-1 activity by anandamide or Delta-9 THC results in increased food intake and weight gain in multiple species including humans (Williams and Kirkham, *Psychopharm.*, 143, 315-317 (1999)). Genetic knock-out of CB-1 result in mice that were hypophagic and lean relative to wild-type litter mates (DiMarzo, et al., *Nature*, 410, 822-825 (2001)). Published studies with CB-1 small molecule antagonists have demonstrated decreased food intake and body weight in rats (Trillou, et. al., *Am. J. Physiol. Regul. Integr. Comp. Physiol.*, R345-R353, (2003)). Chronic administration of the CB-1 antagonist AM-251 for two weeks resulted in substantial body weight reduction and decreased adipose tissue mass (Hildebrandt, et. al., *Eur. J. Pharm*, 462, 125-132 (2003)). There are multiple studies that have assessed the anorexic effect of the Sanofi CB-1 antagonist, SR-141716 (Rowland, et. al., *Pyschopharm.*, 159, 111-116 (2001); Colombo, et. al., *Life Sci.*, 63, 113-117 (1998)). There are at least two CB-1 antagonists in clinical trials for regulation of appetite, Sanofi's SR-141716 and Solvay's SLV-319. Published Phase IIb data reveal that SR-141716 dose-dependently reduced body weight in human subjects over a 16 week trial period. CB-1 antagonists have also been shown to promote cessation of smoking behavior. Phase II clinical data on smoking cessation were presented in September of 2002 at Sanofi-Synthelabo's Information meeting. This data showed that 30.2% of patients treated with the highest dose of SR-141716 stayed abstinent from cigarette smoke relative to 14.8% for placebo.

Compounds that reportedly bind to the cannabinoid G-protein receptors are disclosed in European Patent Documents Nos. EP 0570920 and EP 0444451; International Publications Nos. WO 9729079, WO 9902499, WO 9841519, WO 9412466, WO 03007887, WO 03027069, WO 03027114, WO 03020217, WO 03027076, WO 03035005, WO 03051850, WO 03051851; U.S. Pat. Nos. 4,371,720, 5,081,122, 5,292,736, and 5,013,387; and French Patent No. FR 2,735,774, each of which is incorporated herein by reference.

SUMMARY OF THE INVENTION

In accordance with illustrative embodiments and demonstrating features of the present invention, compounds, pharmaceutical compositions containing the compounds and methods of treatment utilizing the compounds are provided which are capable of modulating the function of cannabinoid receptors. The compounds have the general formula I

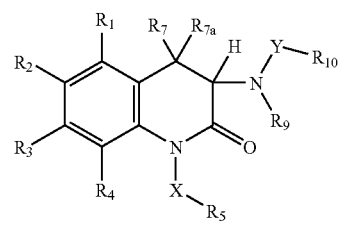

including all pharmaceutically acceptable salts and stereoisomers, wherein $R_1$, $R_2$, $R_3$, $R_4$, $R_5$, $R_7$, $R_{7a}$, $R_9$, $R_{10}$, X and Y are described herein.

DETAILED DESCRIPTION OF THE INVENTION

Thus, in a first embodiment, the present invention provides for a compound of formula I

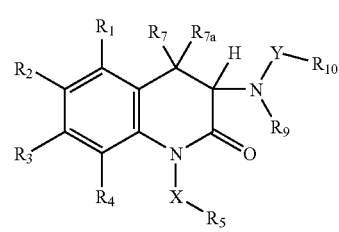

including all pharmaceutically acceptable salts and stereoisomers, wherein:

$R_1$, $R_3$ and $R_4$ are each independently selected from the group consisting of hydrogen, alkyl, halo and CN;

$R_2$ is selected from the group consisting of hydrogen, alkyl, alkenyl, alkynyl, cycloalkyl, cycloalkylalkyl, heterocyclyl, heterocycloalkyl, aryl, heteroaryl, arylalkyl, heteroarylalkyl, acyl, halo, $CF_3$, CN, nitro, $OR_{11}$, $OCF_2H$, $OCF_3$, $NR_{12}R_{12a}$, $COOR_{12}$ and $CONR_{12}R_{12a}$;

$R_5$ is selected from the group consisting of alkyl, alkenyl, alkynyl, cycloalkyl, heterocyclyl, aryl, heteroaryl, $COOR_{13}$ and $CONR_{13}R_{13a}$;

$R_7$ and $R_{7a}$ are each independently selected from the group consisting of hydrogen, alkyl and cycloalkyl;

$R_9$ is selected from the group consisting of hydrogen, alkyl, alkenyl, alkynyl, cycloalkyl, cycloalkylalkyl, heterocyclyl, heterocycloalkyl, arylalkyl and heteroarylalkyl;

$R_{10}$ is selected from the group consisting of alkyl, alkenyl, alkynyl, cycloalkyl, cycloalkylalkyl, heterocyclyl, heterocycloalkyl, aryl, heteroaryl, arylalkyl and heteroarylalkyl;

$R_{11}$ is selected from the group consisting of hydrogen, alkyl, alkenyl, alkynyl, cycloalkyl, cycloalkylalkyl, heterocyclyl, heterocycloalkyl, aryl, heteroaryl, arylalkyl and heteroarylalkyl;

$R_{12}$ and $R_{12a}$ are each independently selected from the group consisting of hydrogen, alkyl, alkenyl, alkynyl, cycloalkyl, cycloalkylalkyl, heterocyclyl, heterocycloalkyl, aryl, heteroaryl, arylalkyl and heteroarylalkyl;

or $R_{12}$ and $R_{12a}$ taken together can form cycloalkyl or heterocyclyl;

$R_{13}$ and $R_{13a}$ are each independently selected from the group consisting of hydrogen, alkyl, alkenyl, alkynyl, cycloalkyl, cycloalkylalkyl, heterocyclyl, heterocycloalkyl, aryl, heteroaryl, arylalkyl and heteroarylalkyl;

or $R_{13}$ and $R_{13a}$ taken together can form cycloalkyl or heterocyclyl;

X is $—(CR_{14}R_{14a})_n—$;

Y is independently selected from the group consisting of $—S(O)_2—$ and $—SO_2N(R_{15})—$;

$R_{14}$ and $R_{14a}$ are each independently selected from the group consisting of hydrogen and alkyl;

$R_{15}$ is selected from the group consisting of hydrogen, alkyl, alkenyl, alkynyl, cycloalkyl, cycloalkylalkyl, heterocyclyl, heterocycloalkyl, aryl, heteroaryl, arylalkyl and heteroarylalkyl;

or $R_{10}$ and $R_{15}$ taken together can form cycloalkyl or heterocyclyl; and n is an integer 0, 1 or 2.

In a preferred embodiment, the present invention provides the compound of formula I, including all pharmaceutically acceptable salts and stereoisomers, wherein:

$R_2$ is selected from the group consisting of aryl, heteroaryl, arylalkyl, halo, $CF_3$, CN, $OR_{11}$, $OCF_2H$ and $OCF_3$;

$R_5$ is selected from the group consisting of aryl and heteroaryl;

$R_9$ is hydrogen;

$R_{10}$ is selected from the group consisting of aryl, heteroaryl, arylalkyl and heteroarylalkyl; and X is $CH_2$.

In a more preferred embodiment, the present invention provides the compound of formula I, including all pharmaceutically acceptable salts and stereoisomers, wherein:

$R_1$, $R_3$ and $R_4$ are each hydrogen;

$R_5$ is aryl;

$R_7$ and $R_{7a}$ are each hydrogen; and

Y is $—S(O)_2—$.

In a second embodiment, the present invention provides a pharmaceutical composition comprising a compound of formula I and a pharmaceutically acceptable carrier or diluent.

In a third embodiment, the present invention provides a pharmaceutical combination comprising a compound of formula I and a therapeutic agent selected from anti-obesity agents; appetite suppressants; anti-diabetic agents; anti-hyperlipidemia agents; hypolipidemic agents; hypocholesterolemic agents; lipid-modulating agents; cholesterol-lowering agents; HDL-raising agents; lipid-lowering agents; anti-hypertensive agents; agents used to treat sleep disorders; agents used to treat substance abuse and addictive disorders; anti-anxiety agents; anti-depressants; anti-psychotic agents; cognition enhancing agents; agents used to treat cognitive disorders; agents used to treat attention deficit-disorders; agents used to treat Alzheimer's disease; agents used to treat Parkinson's disease; anti-inflammatory agents; agents used to treat neurodegeneration; agents used to treat arteriosclerosis; agents used to treat respiratory conditions; agents used to treat gastrointestinal disorders including bowel and motility disorders; cardiac glycosides; and anti-tumor agents.

In a preferred embodiment, the present invention provides a pharmaceutical combination of a compound of formula I and another therapeutic agent wherein the other therapeutic agent may be administered prior to, simultaneously with, or following the administration of the pharmaceutical composition comprising a compound of formula I.

In another preferred embodiment, the present invention provides a pharmaceutical combination of a compound of formula I and an anti-obesity agent wherein the anti-obesity agent is selected from melanocortin receptor (MC4R) agonists; melanin-concentrating hormone receptor (MCHR) antagonists; growth hormone secretagogue receptor (GHSR) antagonists; orexin antagonists; galanin receptor modulators, CCK agonists; GLP-1 agonists and other Pre-proglucagon-derived peptides; NPY1 or NPY5 antagonists; NPY2 and NPY4 modulators; corticotropin releasing factor agonists; histamine receptor-3 (H3) modulators; aP2 inhibitors; PPAR gamma modulators; PPAR delta modulators; acetyl-CoA carboxylase (ACC) inhibitors, adiponectin receptor modulators, 11-β-HSD inhibitors, beta 3 adrenergic agonists, including AJ9677, L750355 and CP331648 or other known beta 3 agonists; thyroid receptor beta modulator; lipase inhibitors, including orlistat and ATL-962; serotonin receptor agonists, including BVT-933; monoamine reuptake inhibitors or releasing agents, including fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine and mazindol; anorectic agents, including topiramate; ciliary neurotrophic factor, including Axokine; brain-derived neurotrophic factor; leptin and leptin modulators; other cannabinoid-1 receptor antagonists, including SR-141716 and SLV-319.

In a fourth embodiment, the present invention provides a method for the treatment or prevention of diseases and disorders associated with G-protein coupled cannabinoid receptor activity, which comprises administering to a mammalian species in need of treatment a therapeutically effective amount of a compound of formula I.

In a preferred embodiment, the present invention provides a method for the treatment of diseases or disorders associated with the activity of the CB-1 receptor, which comprises administering to a mammalian species in need of treatment a therapeutically effective amount of a compound of formula I.

In another preferred embodiment, the present invention provides a method for the treatment of bulimia, obesity or any disease resulting in the patient becoming overweight, which comprises administering to a mammalian species in need of treatment a therapeutically effective amount of a compound of formula I.

In another preferred embodiment, the present invention provides a method for the treatment of metabolic disorders, eating disorders and appetitive disorders, including treatment of the conditions associated with those disorders, such as obesity, diabetes, arteriosclerosis, hypertension, polycystic ovary disease, cardiovascular disease, osteoarthritis, dermatological disorders, hypertension, insulin resistance, hypercholesterolemia, reduced HDL, hypertriglyceridemia, cholelithiasis and sleep disorders, hyperlipidemic conditions, bulimia nervosa and compulsive eating disorders, which comprises administering to a mammalian species in need of treatment a therapeutically effective amount of a compound of formula I.

In another preferred embodiment, the present invention provides a method for the treatment of obesity due to genetic or environmental causes, including overeating and bulimia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure, which comprises administering to a mammalian species in need of treatment a therapeutically effective amount of a compound of formula I.

The following definitions apply to the terms as used throughout this specification, unless otherwise limited in specific instances.

As used herein, the term "alkyl" denotes branched or unbranched hydrocarbon chains containing 1 to 20 carbons, preferably 1 to 12 carbons, and more preferably 1 to 8 carbons, in the normal chain, such as, methyl, ethyl, propyl, isopropyl, butyl, sec-butyl, iso-butyl, tert-butyl, pentyl, hexyl, isohexyl, heptyl, 4,4-dimethylpentyl, octyl, 2,2,4-trimethylpentyl and the like. Further, alkyl groups, as defined herein, may optionally be substituted on any available carbon atom with one or more functional groups commonly attached to such chains, such as, but not limited to hydroxyl, halo, haloalkyl, cyano, mercapto, alkylthio, heterocyclyl, aryl, heteroaryl, carboxyl, carbalkoyl, carboxamido, carbonyl, alkyl, alkenyl, alkynyl, nitro, amino, alkoxyl, aryloxyl, heteroaryloxyl, amido, and the like to form alkyl groups such as trifluoromethyl, 3-hydroxyhexyl, 2-carboxypropyl, 2-fluoroethyl, carboxymethyl, cyanobutyl and the like.

Unless otherwise indicated, the term "alkenyl" as used herein by itself or as part of another group refers to straight or branched chain radicals of 2 to 20 carbons, preferably 2 to 12 carbons, and more preferably 2 to 8 carbons with one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Further, alkenyl groups, as defined herein, may optionally be substituted on any available carbon atom with one or more functional groups commonly attached to such chains, such as, but not limited to halo, haloalkyl, alkyl, alkoxy, alkynyl, aryl, arylalkyl, cycloalkyl, amino, hydroxyl, heteroaryl, cycloheteroalkyl, alkanoylamino, alkylamido, arylcarbonylamino, nitro, cyano, mercapto, and alkylthio.

Unless otherwise indicated, the term "alkynyl" as used herein by itself or as part of another group refers to straight or branched chain radicals of 2 to 20 carbons, preferably 2 to 12 carbons and more preferably 2 to 8 carbons with one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. Further, alkynyl groups, as defined herein, may optionally be substituted on any available carbon atom with one or more functional groups commonly attached to such chains, such as, but not limited to halo, haloalkyl, alkyl, alkoxy, alkenyl, aryl, arylalkyl, cycloalkyl, amino, hydroxyl, heteroaryl, cycloheteroalkyl, alkanoylamino, alkylamido, arylcarbonylamino, nitro, cyano, mercapto, and alkylthio.

Unless otherwise indicated, the term "cycloalkyl" as employed herein alone or as part of another group includes saturated or partially unsaturated (containing one or more double bonds) cyclic hydrocarbon groups containing 1 to 3 rings, appended or fused, including monocyclicalkyl, bicyclicalkyl and tricyclicalkyl, containing a total of 3 to 20 carbons forming the rings, preferably 3 to 10 carbons, forming the rings and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

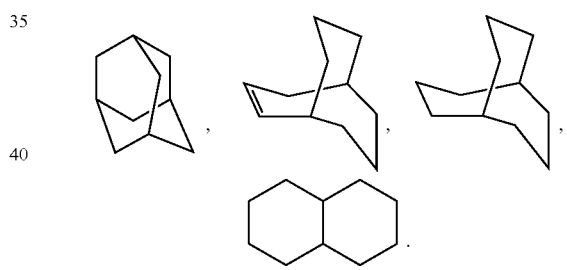

Further, any cycloalkyl may be optionally substituted through any available carbon atoms with one or more groups selected from the group consisting of hydrogen, halo, haloalkyl, alkyl, alkoxy, haloalkyloxy, hydroxyl, alkenyl, alkynyl, aryl, aryloxy, heteroaryl, heteroaryloxy, arylalkyl, heteroarylalkyl, alkylamido, alkanoylamino, oxo, acyl, arylcarbonylamino, amino, nitro, cyano, mercapto, and alkylthio.

The term "cycloalkylalkyl" as used herein alone or as part of another group refers to alkyl groups as defined above having a cycloalkyl substituent, wherein said "cycloalkyl" and/or "alkyl" groups may optionally be substituted as defined above.

Unless otherwise indicated, the term "aryl" as employed herein alone or as part of another group refers to monocyclic and bicyclic aromatic groups containing 6 to 10 carbons in the ring portion (such as phenyl, 1-naphthyl and 2-naphthyl) and may optionally include one to three additional carbocyclic or heterocyclic fused rings, for example

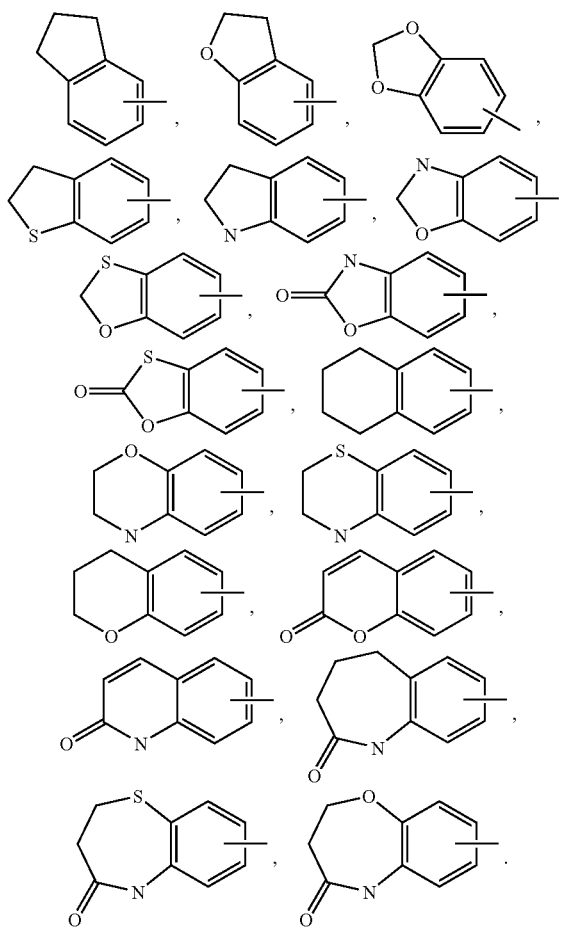

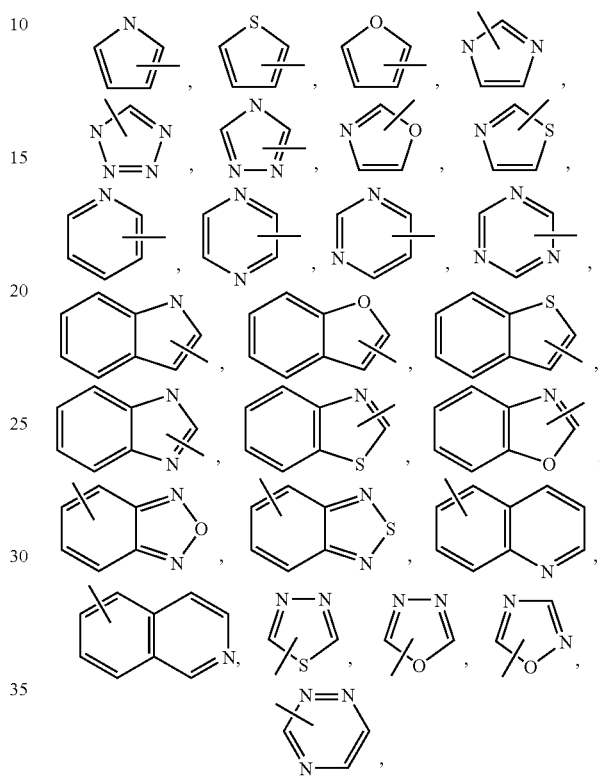

and the like.

Further, "aryl", as defined herein, may optionally be substituted with one or more functional groups, such as halo, alkyl, alkenyl, alkynyl, cycloalkyl, cycloalkylalkyl, heterocyclyl, heterocycloalkyl, aryl, heteroaryl, arylalkyl, arylalkenyl, heteroarylalkyl, heteroarylalkenyl, haloalkyl, $CF_3$, hydroxy, alkoxy, haloalkoxy, $OCF_3$, $OCF_2H$, aryloxy, heteroaryloxy, arylalkoxy, alkylcarbonyloxy, arylcarbonyloxy, aryloxyalkyl, alkylcarbonyl, arylcarbonyl, alkoxycarbonyl, aminocarbonyl, alkylaminocarbonyl, arylaminocarbonyl, aminocarbonylaryl, heteroarylheteroaryl, nitro, cyano, arylazo, amino, substituted amino wherein the amino includes 1 or 2 substituents (which are alkyl or aryl), alkylcarbonylamino, arylcarbonylamino, alkylsulfonylamino, arylsulfonylamino, mercapto, alkylthio, arylthio, alkoxyarylthio, heteroarylthio, arylsulfinyl, alkylsulfonyl, arylsulfonyl, arylthioalkyl, arylsulfinylalkyl, arylsulfonylalkyl, alkylsulfonylalkyl, or arylsulfonaminocarbonyl.

Unless otherwise indicated, the term "heteroaryl" as used herein alone or as part of another group refers to a 5- or 6-membered aromatic ring which includes 1, 2, 3 or 4 heteroatoms such as nitrogen, oxygen or sulfur. Such rings may be fused to an aryl, cycloalkyl, heteroaryl or heterocyclyl group and include possible N-oxides as described in Katritzky, A. R. and Rees, C. W., eds. *Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature* 1982-1995 1996, Elsevier Science, Inc., Tarrytown, N.Y.; and references therein. Further, "heteroaryl", as defined herein, may optionally be substituted with one or more substituents such as the substituents included above in the definition of "substituted alkyl" and "substituted aryl". Examples of heteroaryl groups include the following:

The term "heteroarylalkyl" as used herein alone or as part of another group refers to alkyl groups as defined above having a heteroaryl substituent, wherein said heteroaryl and/or alkyl groups may optionally be substituted as defined above.

The term "heterocyclo", "heterocycle", "heterocyclyl" or "heterocyclic ring", as used herein, represents an unsubstituted or substituted stable, 4 to 7-membered monocyclic ring system which may be saturated or unsaturated, and which consists of carbon atoms, with one to four heteroatoms selected from the group consisting of nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl and other heterocycles described in Katritzky, A. R. and Rees, C. W., eds.

*Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature* 1982-1995 1996, Elsevier *Science, Inc., Tarrytown, N.Y.; and references therein.*

The term "heterocycloalkyl" as used herein alone or as part of another group refers to alkyl groups as defined above having a heterocyclyl substituent, wherein said heterocyclyl and/or alkyl groups may optionally be substituted as defined above.

The terms "arylalkyl", "arylalkenyl" and "arylalkynyl" as used alone or as part of another group refer to alkyl, alkenyl and alkynyl groups, respectively, as defined above having an aryl substituent as defined above. Representative examples of arylalkyl include, but are not limited to, benzyl, 2-phenylethyl, 3-phenylpropyl, benzhydryl and naphthylmethyl and the like.

The terms "alkoxy", "aryloxy", "heteroaryloxy", "arylalkyloxy" or "heteroarylalkyloxy" as employed herein alone or as part of another group include, respectively, alkyl, aryl, heteroaryl, arylalkyl and heteroarylalkyl groups as defined above linked through an oxygen atom.

The term "halogen" or "halo" as used herein alone or as part of another group refers to chlorine, bromine, fluorine, and iodine, with bromine, chlorine or fluorine being preferred.

The term "cyano," as used herein alone or as part of another group, refers to a —CN group.

The term "methylene," as used herein alone or as part of another group, refers to a —$CH_2$— group.

The term "nitro," as used herein alone or as part of another group, refers to a —$NO_2$ group.

The term "acyl", as employed herein alone or as part of another group includes, alkyl, aryl, heteroaryl, arylalkyl and heteroarylalkyl groups as defined above linked through a carbonyl group.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by a halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid or lysine or arginine, or such as benzoic acid, or with organic sulfonic acids, such as ($C_1$-$C_4$) alkyl or arylsulfonic acids which are unsubstituted or substituted, for example by a halogen, for example methanesulfonic acid or p-toluenesulfonic acid. Corresponding acid addition salts can also be formed having, if desired, an additionally present basic center. The compounds of formula I having at least one acid group (for example COOH) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethylpropylamine, or a mono, di or tri-hydroxy(lower)alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate, nitrate and acetate salts.

Preferred salts of the compounds of formula I which contain an acid group include sodium, potassium and magnesium salts and pharmaceutically acceptable organic amine salts.

The term "modulator" refers to a chemical compound with capacity to either enhance (e.g., "agonist" activity) or partially enhance (e.g., "partial agonist" activity) or inhibit (e.g., "antagonist" activity or inverse agonist activity) a functional property or biological activity or process (e.g., enzyme activity or receptor binding); such enhancement or inhibition may be contingent on the occurrence of a specific event, such as activation of a signal transduction pathway, and/or may be manifest only in particular cell types.

The term "prodrug esters" as employed herein includes esters and carbonates formed by reacting one or more hydroxyl group of compounds of formula I with alkyl, alkoxy, or aryl substituted acylating agents employing procedures known to those skilled in the art to generate acetates, pivalates, methylcarbonates, benzoates and the like.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives appears in:

*The Practice of Medicinal Chemistry*, Camille G. Wermuth et al., Ch 31, (Academic Press, 1996);

*Hydrolysis in Drug and Prodrug Metabolism*, Bernard Testa and Joachim M. Mayer, (Wiley-VCH, 2003);

*Design of Prodrugs*, edited by H. Bundgaard, (Elsevier, 1985);

*A Textbook of Drug Design and Development*, P. Krogsgaard-Larson and H. Bundgaard, eds. Ch 5, pp. 113-191 (Harwood Academic Publishers, 1991). Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration.

All stereoisomers of the compounds of the instant invention are contemplated, either in mixture or in pure or substantially pure form. The compounds of the present invention can have asymmetric centers at any of the carbon atoms including those within any of the R substituents.

Consequently, compounds of formula I can exist in enantiomeric or diastereomeric forms or in mixtures thereof. The processes for preparation can utilize racemates, enantiomers or diastereomers as starting materials. In order to prepare diastereomeric or enantiomeric products, conventional methods for isomer separation may be employed. These include, for example, chromatographic techniques, chiral RPLC, fractional crystallization, and sequences of derivatization, separation and de-derivatization.

The compounds of formula I of the invention can be prepared as shown below in the following descriptions and reaction schemes, as well as by using relevant published literature procedures that may be used by one skilled in the art. Exemplary reagents and procedures for these reactions appear hereinafter and in the working Examples.

The following abbreviations may be employed in the descriptions, schemes, working Examples and elsewhere herein:
Ac=acetyl
AcCN or MeCN=acetonitrile
AcOH=acetic acid
Boc=tert-butoxycarbonyl
BINAP=2,2'-bis(diphenylphosphino)-1,1'-binaphthyl
Brine=saturated aqueous sodium chloride solution
Chiralpak®=Trademark of Chiral Technologies, Inc. Eaton, Pa.
DCM=dichloromethane
DIPEA=N,N-diisopropylethylamine
DMF=N,N-dimethylformamide
EDAC=1-(3-Dimethylaminopropyl)-3-ethylcarbodiimide hydrochloride
EtOAc=ethyl acetate
$Et_3N$=triethylamine
$Et_2O$=diethyl ether
$Et_3SiH$=triethylsilane
HOBt=1-hydroxybenzotriazole hydrate
HPLC=high performance liquid chromatography
LAH=lithium aluminum hydride
LG=leaving group such as chloride, bromide, methanesulfonate or trifluoromethanesulfonate.
MeOH=methanol
MS or Mass Spec=mass spectrometry
$NaB(OAc)_3H$=sodium triacetoxyborohydride
NaOH=sodium hydroxide
NMM=N-methylmorpholine
PG=protecting group
PXPd=dichlorobis(chlorodi-tert-butylphosphine)palladium
RT=room temperature
TFA=trifluoroacetic acid
THF=tetrahydrofuran
THQ=tetrahydroquinoline
mp=melting point
min=minute(s)
h=hour(s)
L=liter(s)
mL=milliliter(s)
μl=microliter(s)
g=gram(s)
mg=milligram(s)
mol=mole(s)
mmol=millimole(s)
nM=nanomolar Compounds of formula I wherein Y is —$S(O)_2$— may be prepared by coupling sulfonylating agents of formula II with amines of formula III using standard methods for sulfonamide formation, as known to those skilled in the art, for example, by combining equimolar amounts of amine III and compound II, typically a sulfonyl chloride, in dichloromethane solution at room temperature in the presence of a base such as triethylamine. Sulfonylating agents II can be obtained commercially, are known, or may be prepared according to the routes and procedures described in Hamada, et al., *Synthesis*, 852-854 (1986) or by other methods know to those skilled in the art.

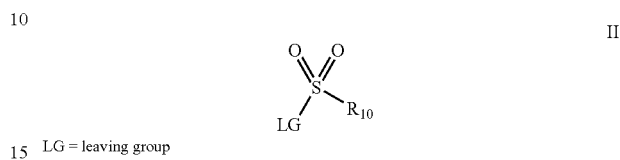

LG = leaving group

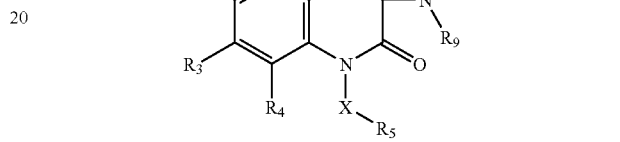

Compounds of formula I wherein Y is —$SO_2N(R_{15})$— may be prepared by coupling amines of formula III with sulfamoylating agents of formula IV using standard methods for sulfamide formation, as known to those skilled in the art, for example, by combining equimolar amounts of amine III and compound IV, in which the leaving group (LG) is typically chlorine, in dichloromethane solution at room temperature in the presence of a base such as triethylamine. The compounds of formula IV may also contain atypical leaving groups such as an oxazolidinone as described in Ducry, et al., *Helvetica Chimica Acta*, 82, 2432-2447 (1999) or a catechol as described in Lee, et al., *Bull. Korean Chem. Soc.*, 14, 762-764 (1993).

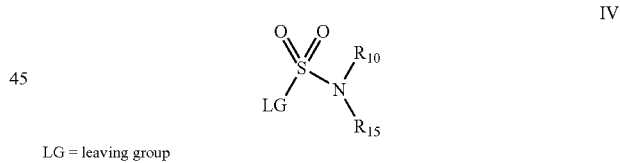

LG = leaving group

Sulfamoylating agents IV can be obtained commercially, are known, or may be prepared according to the routes and procedures described in Ducry, et al., *Helvetica Chimica Acta*, 82, 2432-2447 (1999) and Lee, et al., *Bull. Korean Chem. Soc.*, 14, 762-764 (1993) or by other methods know to those skilled in the art, such as reaction of amines $HNR10R_{15}$ with sulfuryl chloride (see for example Padma, et al., *J Fluorine Chem.*, 20, 425-438 (1982)).

Furthermore, the formation of the sulfamide linkage of compounds of formula I wherein Y is —$SO_2N(R_{15})$— may also be accomplished by coupling compounds of formula IV' with amines $HNR10R_{15}$. The compounds of formula IV' are available from analogous amines of formula III by the methods described in Ducry, et al., *Helvetica Chimica Acta*, 82, 2432-2447 (1999) and Lee, et al., *Bull. Korean Chem. Soc.*, 14, 762-764 (1993).

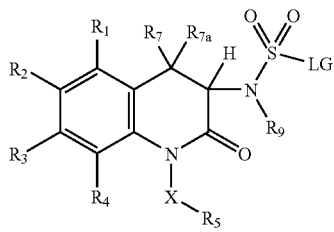

IV'

Amines of formula III are known or may be prepared by deprotection of the corresponding protected amines V in which the amino group is protected with a monovalent protecting group. Monovalent protecting groups include, for example, carbamates, amides, and N-benzyl derivatives. These and other standard amine protecting groups, as well as methods for their introduction and removal, are described in Protective Groups in Organic Synthesis (2nd Edition, T. W. Greene and P. G. M. Wuts, John Wiley & Sons, 1991).

V

Additionally, amines IIIa, defined as the subset of amines III wherein $R_9$ is hydrogen, may be prepared by the procedures and methods disclosed in US 2004/002495 or references contained therein, or by analogy to the procedures and methods disclosed in US 2004/002495 or references contained therein, or by deprotection of protected amines VI in which the amino group is protected with a divalent protecting group. Divalent protecting groups include, for example phthalimides. These and other standard amine protecting groups, as well as methods for their introduction and removal, are described in Protective Groups in Organic Synthesis ($2^{nd}$ Edition, T. W. Greene and P. G. M. Wuts, John Wiley & Sons, 1991). Amines IIIa, may also be prepared by deprotection of the subset of protected amines V in which $R_9$ is hydrogen (see XVI below).

IIIa

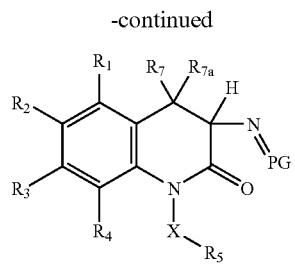

VI

Protected amines V and VI may be prepared from compounds of formula VII and VIII, respectively, by alkylation with a compound of formula IX following the procedures and methods disclosed in US 2004/002495 or references contained therein, or by analogy to the procedures and methods disclosed in US 2004/002495 or references contained therein. For example, compounds of formula V wherein $XR_5$ represents benzyl may be prepared by alkylation of the analogous compounds of formula VII with benzyl bromide at room temperature in a solvent such as N,N-dimethylformamide in the presence of a base such as cesium carbonate.

VII

VIII

IX

Protected amines VII wherein $R_9$ is hydrogen (see XVII below) and protected amines VIII may be prepared following the procedures and methods disclosed in US 2004/002495 or references contained therein, or by analogy to the procedures and methods disclosed in US 2004/002495 or references contained therein.

Amines III wherein $R_9$ is not hydrogen may also be prepared from the analogous amines IIIa by either alkylation with a compound of formula X or by reductive amination with a carbonyl compound of formula XI, both of which methods are known to those skilled in the art. For example, amines III in which $R_9$ is methyl may be prepared by alkylation of the analogous amines of formula IIIa by treatment with methyl iodide in a solvent such as tetrahydrofuran at room temperature in the presence of a base such as sodium hydride. Alternatively, the same transformation may be accomplished by reductive amination in which the amine of formula IIIa is treated with formaldehyde at room temperature in a solvent such as ethanol in the presence of an acid such as acetic acid and a reducing agent such as sodium cyanoborohydride.

X

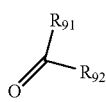

XI $CHR_{91}R_{92} = R_9$

Compounds of formulas IX, X and XI are commercially available, are known, or can be prepared by methods known to those skilled in the art.

Compounds of formula I wherein $R_9$ is not hydrogen may also be prepared from the analogous compounds of formula Ia, defined as the subset of compounds of formula I wherein $R_9$ is hydrogen, by alkylation with a compound of formula X. Standard alkylation conditions known to those skilled in the art may be used. For example, a compound of formula I wherein $R_9$ is methyl may be prepared by treating the analogous compound of formula Ia with methyl iodide in a solvent such as tetrahydrofuran at room temperature in the presence of a base such as sodium hydride.

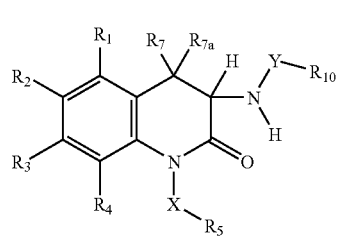

Ia

Compounds of formula I wherein $R_9$ and $R_{15}$ (if present in Y) are not hydrogen may also be prepared from analogous compounds of formula XII by alkylation with compounds of formula IX. Standard alkylation conditions known to those skilled in the art may be used. For example, compounds of formula I wherein $XR_5$ represents benzyl may be prepared by alkylation of the analogous compound of formula XII with benzyl bromide at room temperature in a solvent such as N,N-dimethylformamide in the presence of a base such as cesium carbonate.

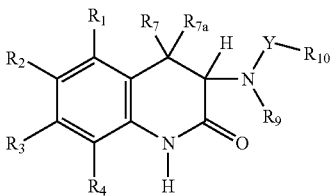

XII

The synthetic pathways described above are diagrammed in Schemes 1 and 2 below with each transformation labeled by reaction class (alkylation, deprotection, etc.). Additional useful synthetic routes are outlined in Schemes 3 to 5 below. The transformations indicated in Schemes 3 to 5 are labeled by reaction class in the same manner as those in Schemes 1 and 2. The details provided above for the reaction classes shown in Schemes 1 and 2 apply to those reaction classes in Schemes 3 to 5 as well.

Scheme 1

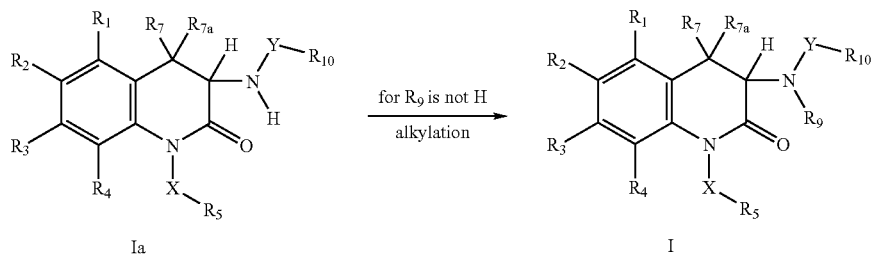

-continued
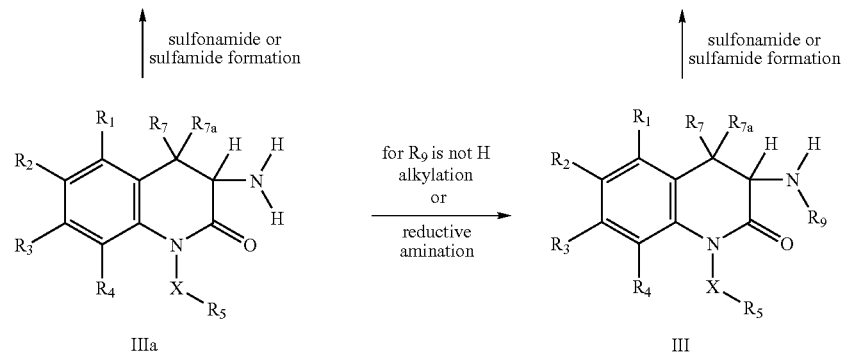
IIIa → III (for R9 is not H alkylation or reductive amination)
Both proceed upward via sulfonamide or sulfamide formation.
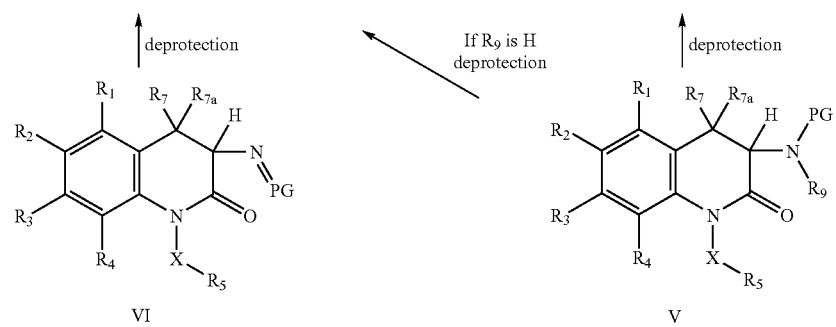
VI ← V (If R9 is H deprotection)
Both proceed upward via deprotection.
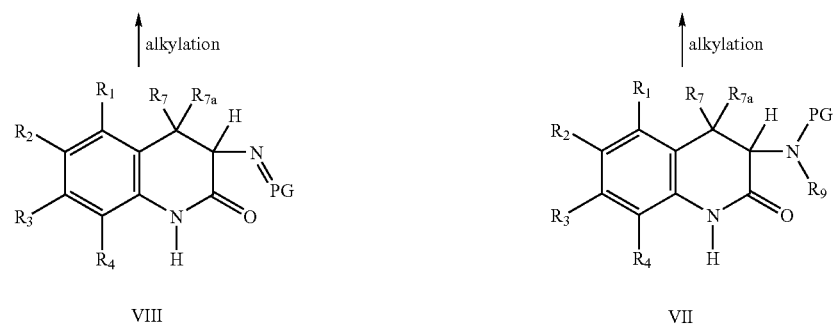
VIII, VII
Both proceed upward via alkylation.
Scheme 2
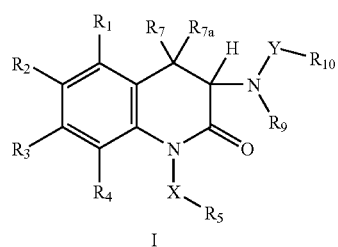
I
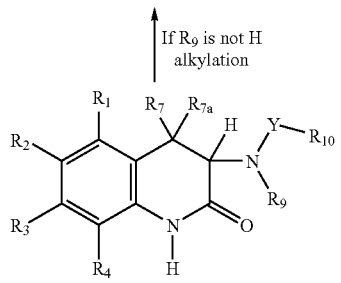
XII
(If R9 is not H alkylation)

Scheme 3
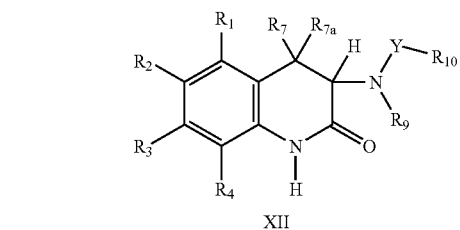
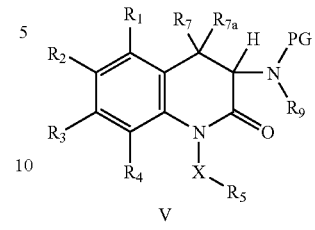
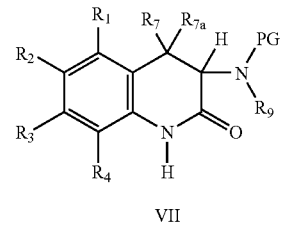
Scheme 4
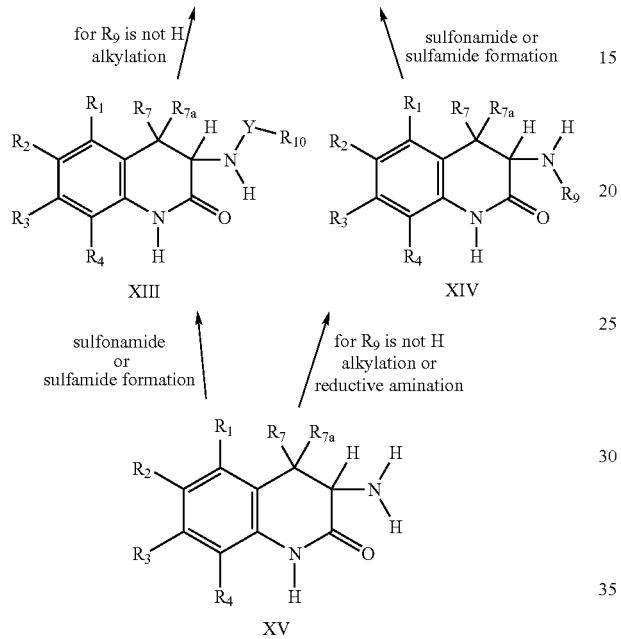
Scheme 5
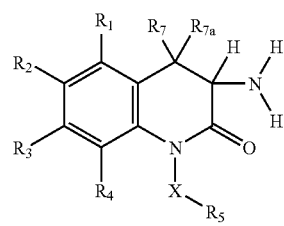
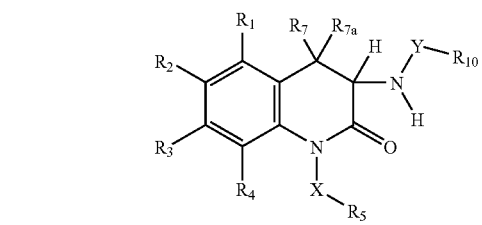
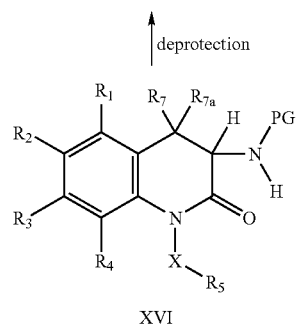
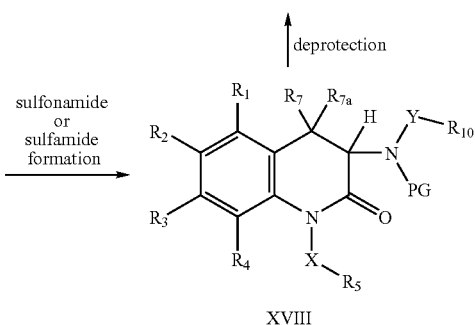

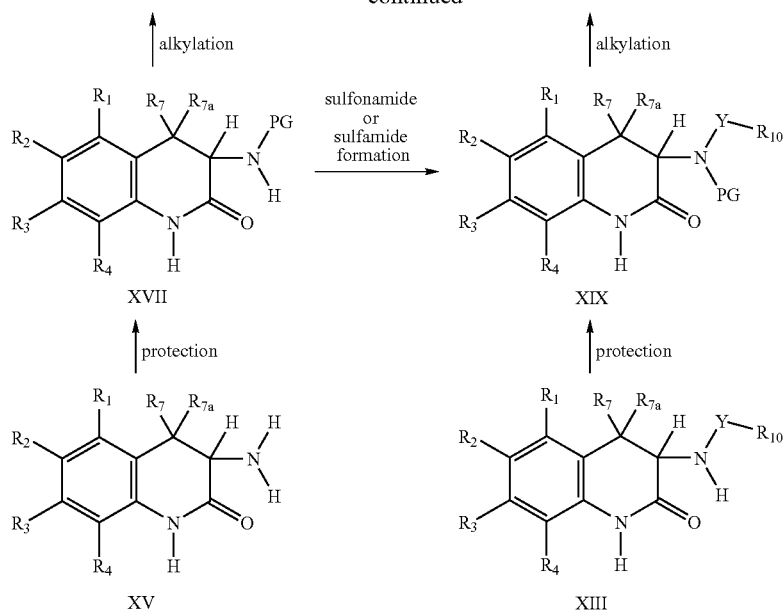

It is understood that the reagents mentioned throughout are example reagents, not meant to be limiting. Those skilled in the art will recognize that there are many acids (trifluoroacetic acid, hydrochloric acid, polyphosphoric acid, etc.), many bases (triethylamine, sodium hydride, potassium methoxide, etc.), many oxidants (hydrogen peroxide, 3-chloroperoxybenzoic acid, etc.), many hydrogenation catalysts (palladium, platinum oxide, Raney® Nickel, etc.), and so on that may be employed to synthesize the compounds of the invention. In some cases alternative reagents known to those skilled in the art will be superior to those specifically mentioned. Alternative reagents may be found in Reagents For Organic Synthesis (Fieser and Fieser, John Wiley & Sons) and Compendium of Organic Synthetic Methods (John Wiley & Sons).

Many compounds of formulas I, Ia, V, VI, VII, VIII, XII, XIII, XVI, XVII, XVIII and XIX wherein $R_1$, $R_2$, $R_3$ or $R_4$ is other than hydrogen, halo or hydroxy, may be prepared from analogous compounds of formulas I, Ia, V, VI, VII, VIII, XII, XIII, XVI, XVII, XVIII and XIX, respectively, wherein $R_1$, $R_2$, $R_3$ or $R_4$ is halo or hydroxy, by using various palladium catalyzed coupling procedures as described in Aranyos, et al., J. Am. Chem. Soc., 121, 4369-4378 (1999) and Hamann, et al., J. Am. Chem. Soc., 120, 7369-7370 (1998) and references contained therein, and in recent papers authored by Gregory C. Fu, Stephen L. Buchwald, or John F. Hartwig. These procedures are directly applicable when $R_1$, $R_2$, $R_3$ or $R_4$ is halo. When $R_1$, $R_2$, $R_3$ or $R_4$ is hydroxy, prior activation by conversion of the hydroxyl group to a trifluoromethylsulfonyloxy group, as described in the aforementioned references, is required. In either case, the new $R_1$, $R_2$, $R_3$ or $R_4$ group is derived from a boronic acid (for example, phenylboronic acid), boronic ester, stannane (for example, 3-thienyltributylstannane) or other organometallic compound (for example, 2-thiazolylzinc bromide) or metal salt (for example, zinc cyanide). An alternate route for accomplishing the conversion of compounds of formulas I, Ia, V, VI, VII, VIII, XII, XIII, XVI, XVII, XVIII and XIX wherein $R_1$, $R_2$, $R_3$ or $R_4$ is halo or hydroxyl to compounds of formulas I, Ia, V, VI, VII, VIII, XII, XIII, XVI, XVII, XVIII and XIX, respectively, wherein $R_1$, $R_2$, $R_3$ or $R_4$ is other than hydrogen, halo or hydroxy entails first conversion of $R_1$, $R_2$, $R_3$ or $R_4$ from a halo or a trifluoromethylsulfonyloxy group to a boron, tin or other metal moiety, followed by palladium catalyzed coupling with a reagent consisting of the desired $R_1$, $R_2$, $R_3$ or $R_4$ group activated by a halo or trifluoromethylsulfonyloxy group. Working Examples 4, 5, 10 and 12 illustrate these conversions.

Along these lines, particularly useful intermediates are compounds of formula XVII in which $R_2$ is bromo, which can be prepared from the analogous compounds of formula XVII in which $R_2$ is hydrogen, by bromination with a brominating agent such as benzyltrimethylammonium tribromide in a solvent such as a MeOH—$CH_2Cl_2$ mixture in the presence of a base such as $CaCO_3$.

In general, the interchange of functional groups within all the various R groups may be accomplished according to the methods and procedures described in Compendium of Organic Synthetic Methods (John Wiley & Sons) and Comprehensive Organic Transformations—A Guide To Functional Group Preparations (R. C. Larock, VCH Publishers, 1989). It is understood that during the course of manipulating any functional group within any of the various R groups, standard protecting groups, as described in Protective Groups in Organic Synthesis, may be employed to avoid undesired reaction of any other functional group.

Standard protecting groups may be used at any stage of synthesis, for example in manipulating a functional group to convert one compound of formula I to another compound of formula I, or in manipulating a functional group to convert one protected amine V to another protected amine V, or to avoid undesired reaction during the conversion of amines III to compounds of formula I, or during the sequence of steps leading to the formation of protected amine V.

The following working Examples serve to better illustrate, but not limit, some of the preferred embodiments of the invention.

EXAMPLE 1

N-(1-Benzyl-2-oxo-1,2,3,4-tetrahydroquinolin-3-yl)-benzenesulfonamide

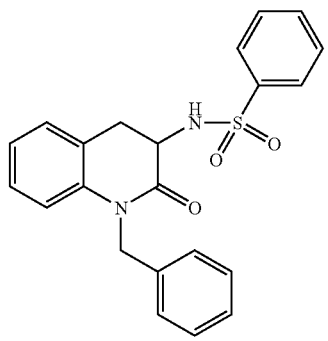

1A. (2-Oxo-1,2,3,4-tetrahydroquinolin-3-yl)-carbamic acid tert-butyl ester

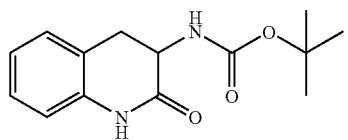

The title compound was prepared from 3-amino-2-oxo-1,2,3,4-tetrahydroquinoline (Davis, A. L., et al., *Arch. Biochem. Bi* according to the procedures described in US 2004/002495.

1B. (1-Benzyl-2-oxo-1,2,3,4-tetrahydroquinolin-3-yl)-carbamic acid tert-butyl ester

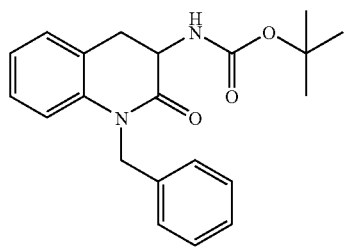

To a solution of 1A (95 mg, 0.36 mmol) in DMF (2 mL) was added $Cs_2CO_3$ (260 mg, 0.8 mmol), followed by benzyl bromide (74 mg, 0.43 mmol). After stirring at RT under argon for 4 h, the mixture was partitioned between water and EtOAc. The aqueous layer was extracted with EtOAc (20 mL). The combined organic layers were washed with brine, dried ($Na_2SO_4$), and evaporated under vacuum. The resulting residue was chromatographed on silica gel (10 g) eluted with 20-30% EtOAc in hexane (step-wise gradient) to obtain the title compound (112 mg, 88%).

1C. 3-Amino-1-benzyl-2-oxo-1,2,3,4-tetrahydroquinoline, Trifluoroacetic Acid Salt

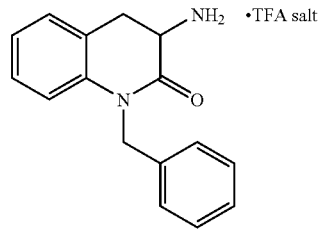

To a solution of 1B (106 mg, 0.30 mmol) in $CH_2Cl_2$ (1 mL) was added TFA (0.8 mL). The mixture was stirred at RT under argon for 2 h, then evaporatated under vacuum to obtain the title compound (75 mg).

1D. N-(1-Benzyl-2-oxo-1,2,3,4-tetrahydroquinolin-3-yl)-benzenesulfonamide

To a solution of 1C (75 mg, 0.30 mmol) in $CH_3CN$ (1.5 mL) was added diisopropylethylamine (0.18 mL, 1.0 mmol), followed by benzenesulfonyl chloride (0.06 mL, 0.3 mmol). After stirring at RT under argon for 1.5 h, the mixture was partitioned between water and EtOAc. The EtOAc layer was washed with water, then brine, dried ($Na_2SO_4$), and evaporatated under vacuum. The resulting residue was chromatographed on silica gel (10 g) eluted with 20-50% EtOAc in hexane (step-wise gradient) to obtain the title compound (51 mg, 43%) as a white solid. HPLC retention time=6.8 min (Zorbax SB 5 micron C18 4.6×75 mm column eluted with a 0% to 100% B solvent gradient over 8 min; solvent A=90% $H_2O$, 10% MeOH, 0.2% $H_3PO_4$ and solvent B=10% $H_2O$, 90% MeOH, 0.2% $H_3PO_4$; flow rate=2.5 mL/min; UV detection at 220 nm). MS (ESI): m/z=393 $[M+H]^+$.

EXAMPLE 2

N-[1-(3-Chlorobenzyl)-2-oxo-1,2,3,4-tetrahydroquinolin-3-yl]-benzenesulfonamide

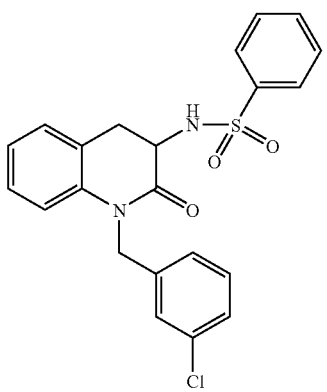

The title compound was prepared from 1A according to the procedures described in 1B, 1C, and 1D, but substituting 3-chlorobenzyl bromide for benzyl bromide in 1B. HPLC retention time=7.1 min (Zorbax SB 5 micron C18 4.6×75 mm column eluted with a 0% to 100% B solvent gradient over 8 min; solvent A=90% $H_2O$, 10% MeOH, 0.2% $H_3PO_4$ and solvent B=10% H₂O, 90% MeOH, 0.2% H₃PO₄; flow rate=2.5 mL/min; UV detection at 220 nm). MS (ESI): m/z=427 [M+H]⁺.

EXAMPLE 3

N-(1-Benzyl-6-bromo-2-oxo-1,2,3,4-tetrahydroquinolin-3-yl)-benzenesulfonamide

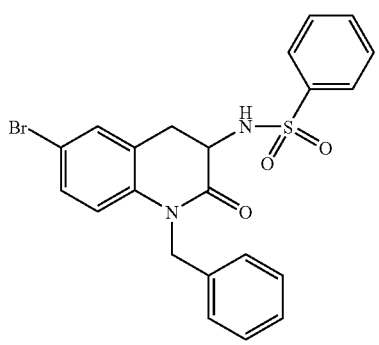

3A.
3-Amino-6-bromo-2-oxo-1,2,3,4-tetrahydroquinoline

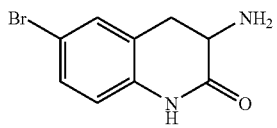

The title compound was prepared from 3-amino-1-hydroxy-2-oxo-1,2,3,4-tetrahydroquinoline hydrochloride (Davis, A. L., et al., *J. Med. Chem.*, 7, 632 (1964)) according to procedures similar to those described in McCord, T. J., et al., *J. Het. Chem.*, 9, 119 (1972), as follows. To 48% aqueous HBr solution (70 mL) was added 3-amino-1-hydroxy-2-oxo-1,2,3,4-tetrahydroquinoline hydrochloride (2.0 g, 9.3 mmol). The resulting mixture was stirred at reflux for 2 h. HPLC/MS indicated a nearly 1:1 mixture of desired product and its 8-bromo isomer plus a small amount of dibromo product. After cooling to RT, precipitate was filtered and treated with excess saturated aqueous Na₂CO₃ solution to make a basic (pH=10) mixture. This heterogenous mixture was extracted repeatedly with CH₂Cl₂. During these extractions, a substantial amount of solid remained undissolved and suspended in the aqueous layer. The combined organic extracts were dried over Na₂SO₄ and evaporated under vacuum. The resulting residue was chromatographed on silica gel eluted with 10% MeOH in CH₂Cl₂ to obtain the title compound (0.15 g). Additional title compound (0.56 g) was obtained by filtering the heterogenous aqueous layer and washing the filtered solid with water, then Et₂O, and then 10% MeOH in Et₂O before drying under vacuum.

3B. (6-Bromo-2-oxo-1,2,3,4-tetrahydroquinolin-3-yl)-carbamic acid tert-butyl ester

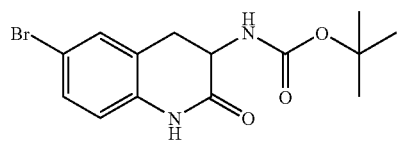

To a stirring solution of 3A (0.56 g, 2.33 mmol) in CH₃CN (15 mL) at RT was added aqueous Na₂CO₃ solution (2.0 M, 5 mL), followed by di-tert-butyl dicarbonate (0.76 g, 3.5 mmol). After 16 h the solvent was largely evaporated under vacuum, water (10 mL) was added, and the resulting mixture was extracted with CH₂Cl₂ (15 mL, 3 times). The combined organic layers were dried (Na₂SO₄) and evaporated to obtain a white solid residue. This solid was triturated with 50% MeOH in Et₂O, then dried under vacuum to obtain the title compound (0.63 g). The filtrate from the trituration was evaporated under vacuum and the residue was chromatographed on silica gel eluted with 15-33% EtOAc in hexane (step-wise gradient) to obtain additional title compound.

3C. (1-Benzyl-6-bromo-2-oxo-1,2,3,4-tetrahydroquinolin-3-yl)-carbamic acid tert-butyl ester

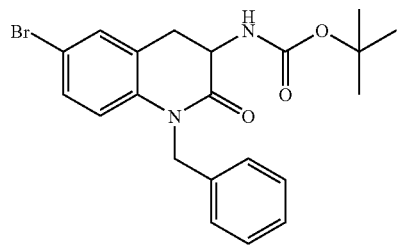

A stirring mixture of 3B (0.60 g, 1.76 mmol), K₂CO₃ (0.49 g, 3.52 mmol), and benzyl bromide (0.36 g, 2.11 mmol) in acetone (15 mL) was heated to reflux under argon for 16 h. The mixture was then cooled to RT and the solvent was evaporated under vacuum. The resulting residue was partitioned between water and EtOAc. The EtOAc layer was washed with brine, dried (Na₂SO₄), and evaporated. The resulting crude product was chromatographed on silica gel eluted with 10-20% EtOAc in hexane (step-wise gradient) to obtain the title compound (0.72 g) as a solid.

3D. 3-Amino-1-benzyl-6-bromo-2-oxo-1,2,3,4-tetrahydroquinoline, hydrochloric Acid salt

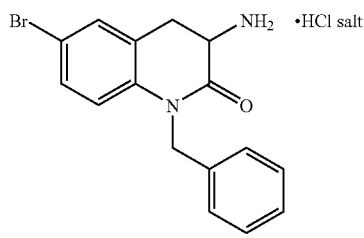

To a solution of 3C (22 mg, 0.05 mmol) in CH$_2$Cl$_2$ (2 mL) was added HCl in 1,4-dioxane solution (4.0 M, 2 mL). The resulting mixture was stirred at RT for 2 h, and then the solvent was evaporated under vacuum. The resulting residue was coevaporated with toluene twice, then CH$_2$Cl$_2$ twice, and dried under vacuum to obtain the title compound, which was used directly in its entirety in the next step.

3E. N-(1-Benzyl-6-bromo-2-oxo-1,2,3,4-tetrahydro-quinolin-3-yl)-benzenesulfonamide To a solution of 3D (0.05 mmol) in CH$_2$Cl$_2$ (2 mL) under argon was added triethylamine (10 mg, 0.10 mmol), followed by benzenesulfonyl chloride (11 mg, 0.06 mmol). After stirring at RT for 16 h, the solvent was evaporated under vacuum, and the resulting residue was coevaporated with toluene, then MeOH. Crude product thus obtained was purified by reverse phase preparative HPLC employing an octadecyl sulfate (C-18) column eluted with a solvent gradient of solvents A and B, starting with at least 20% of solvent B and finishing with 100% of solvent B (solvent A=90% H$_2$O, 10% MeOH, 0.1% TFA and solvent B=10% H$_2$O, 90% MeOH, 0.1% TFA). This provided the title compound (6.7 mg) as a white solid. HPLC/MS retention time=3.7 min (Phenomenex Luna 5 micron C18 4.6 mm×50 mm column eluted with a 0% to 100% B solvent gradient over 4 min; solvent A=90% H$_2$O, 10% MeOH, 0.1% TFA and solvent B=10% H$_2$O, 90% MeOH, 0.1% TFA; flow rate=4.0 mL/min; UV detection at 220 nm); m/z=471 and 473 [M+H]$^+$, 493 and 495 [M+Na]$^+$.

EXAMPLE 4

N-(1-Benzyl-2-oxo-6-phenyl-1,2,3,4-tetrahydro-quinolin-3-yl)-benzenesulfonamide

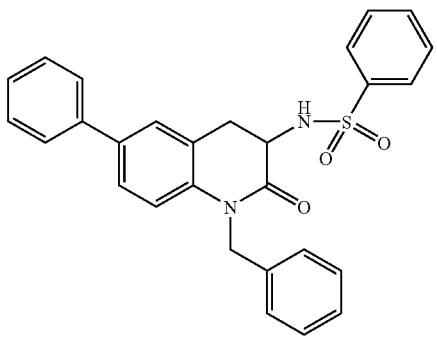

4A. (1-Benzyl-2-oxo-6-tributylstannyl-1,2,3,4-tetrahydroquinolin-3-yl)-carbamic acid tert-butyl ester

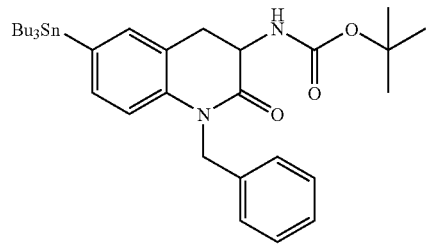

To a solution of 3C (0.60 g, 1.4 mmol) in degassed toluene (5 mL) was added tetrakis(triphenylphosphine)palladium (81 mg, 0.07 mmol) and hexabutylditin (1.9 g, 4.2 mmol). The resulting mixture was heated at 80° for 16 h under argon. After cooling to RT, the solvent was evaporated under vacuum, and the residue was chromatographed on silica gel eluted with 13% EtOAc in hexane to obtain the title compound (0.53 g) as a gum.

4B. (1-Benzyl-2-oxo-6-phenyl-1,2,3,4-tetrahydro-quinolin-3-yl)-carbamic acid tert-butyl ester

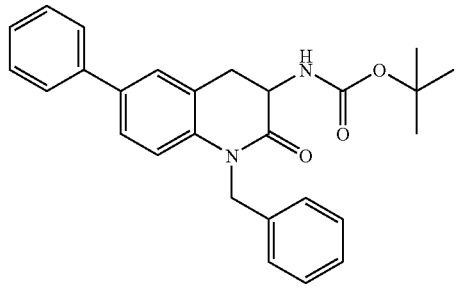

To a solution of 4A (58 mg, 0.10 mmol) in degassed THF (1 mL) was added tetrakis(triphenylphosphine)palladium (12 mg, 0.01 mmol), triphenylphosphine oxide (28 mg, 0.10 mmol), K$_2$CO$_3$ (14 mg, 0.10 mmol), and bromobenzene (47 mg, 0.30 mmol). The resulting mixture was heated at 80° for 16 h under argon. After cooling to RT, the mixture was diluted with a 90% MeOH in H$_2$O solution and filtered. The filtrate was directly injected to reverse phase preparative HPLC employing an octadecyl sulfate (C-18) column eluted with a solvent gradient of solvents A and B, starting with at least 20% of solvent B and finishing with 100% of solvent B (solvent A=90% H$_2$O, 10% MeOH and solvent B=10% H$_2$O, 90% MeOH). This provided the title compound (24 mg).

4C. N-(1-Benzyl-2-oxo-6-phenyl-1,2,3,4-tetrahydro-quinolin-3-yl)-benzenesulfonamide The title compound (15 mg) was prepared from 4B (22 mg) according to the procedures described in 3D and 3E. HPLC/MS retention time=4.0 min (Phenomenex Luna 5 micron C18 4.6 mm×50 mm column eluted with a 0% to 100% B solvent gradient over 4 min; solvent A=90% H$_2$O, 10% MeOH, 0.1% TFA and solvent B=10% H$_2$O, 90% MeOH, 0.1% TFA; flow rate=4.0 mL/min; UV detection at 220 nm); m/z=469 [M+H]$^+$, 491 [M+Na]$^+$.

EXAMPLE 5

N-(1,6-Dibenzyl-2-oxo-1,2,3,4-tetrahydroquinolin-3-yl)-benzenesulfonamide

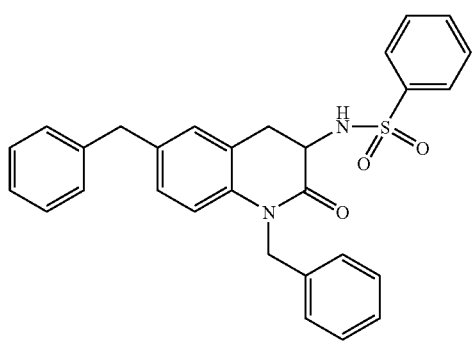

The title compound (9 mg) was prepared from 4A (58 mg) according to the procedures described in 4B, 3D, and 3E, but substituting benzyl bromide for bromobenzene in 4B (10 mg of product was obtained in this first step after reverse phase preparative HPLC). HPLC/MS retention time=4.0 min (Phenomenex Luna 5 micron C18 4.6 mm×50 mm column eluted with a 0% to 100% B solvent gradient over 4 min; solvent A=90% $H_2O$, 10% MeOH, 0.1% TFA and solvent B=10% $H_2O$, 90% MeOH, 0.1% TFA; flow rate=4.0 mL/min; UV detection at 220 nm); m/z=483 $[M+H]^+$, 505 $[M+Na]^+$.

EXAMPLE 6

(R)—N-(1-Benzyl-6-bromo-2-oxo-1,2,3,4-tetrahydroquinolin-3-yl)-benzeesulfonamide

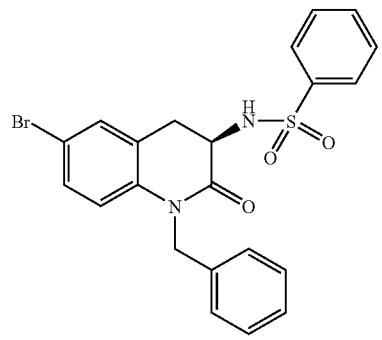

6A. (R)-(6-Bromo-2-oxo-1,2,3,4-tetrahydroquinolin-3-yl)-carbamic acid tert-butyl ester Also isolated: (S)-(6-Bromo-2-oxo-1,2,3,4-tetrahydroquinolin-3-yl)-carbamic acid tert-butyl ester

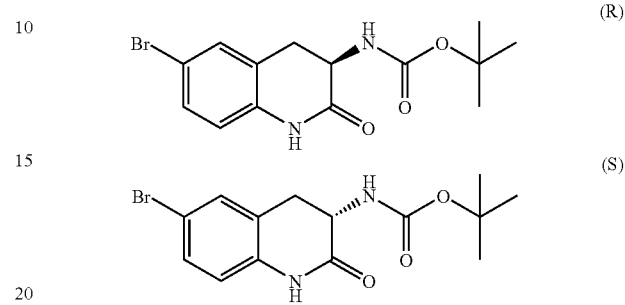

Preparative enantiomeric separation of 3B (0.37 g) was achieved by chiral normal phase HPLC on a 50 mm×250 mm Chiralcel AD column eluted with 7.5% MeOH, 7.5% EtOH, 85% heptane. The R isomer, 6A (0.17 g), eluted before the S isomer (0.16 g). Both were obtained in>99% ee. Stereochemical assignment was ultimately proven by x-ray crystal structure of Example 7, which was derived from 6A.

6B. (R)-(1-Benzyl-6-bromo-2-oxo-1,2,3,4-tetrahydroquinolin-3-yl)-carbamic acid tert-butyl ester

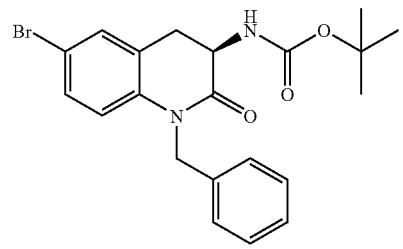

The title compound was prepared from 6A according to the procedures described in 3C.

6C. (R)-3-Amino-1-benzyl-6-bromo-2-oxo-1,2,3,4-tetrahydroquinoline, hydrochloric acid salt

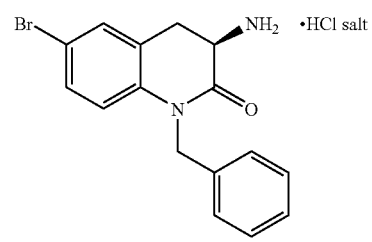

The title compound was prepared from 6B according to the procedures described in 3D.

6D. (R)-N-(1-Benzyl-6-bromo-2-oxo-1,2,3,4-tetrahydroquinolin-3-yl)-benzenesulfonamide The title compound was prepared from 6C according to the procedures described in 3E, except that in this case the title compound was purified by silica gel chromatography rather than preparative HPLC. The reaction mixture was loaded directly onto a silica gel column, which was eluted with 100% CH$_2$Cl$_2$. HPLC/MS retention time=3.8 min (Phenomenex Luna 5 micron C18 4.6 mm×50 mm column eluted with a 0% to 100% B solvent gradient over 4 min; solvent A=90% H$_2$O, 10% MeOH, 10 mM NH$_4$OAc and solvent B=10% H$_2$O, 90% MeOH, 10 mM NH$_4$OAc; flow rate=4.0 mL/min; UV detection at 220 nm); m/z=471 and 473 [M+H]$^+$, 469 and 471 [M−H]$^−$.

EXAMPLE 7

(R)-N-(1-Benzyl-6-bromo-2-oxo-1,2,3,4-tetrahydroquinolin-3-yl)-3,5-difluorobenzenesulfonamide

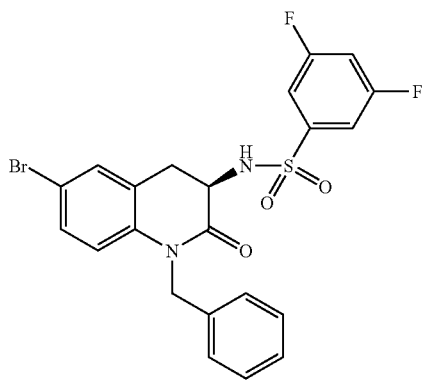

To a solution of 6C (0.068 mmol) in CH$_2$Cl$_2$ (11 mL) under argon was added triethylamine (36 mg, 0.36 mmol), followed by 3,5-difluorobenzenesulfonyl chloride (24 mg, 0.113 mmol). After stirring at RT for 4 h, the reaction mixture was loaded directly onto silica gel and chromatographed by elution with 100% CH$_2$Cl$_2$. The title compound (32 mg) was obtained as a white solid. Stereochemical assignment was proven by x-ray crystal structure. HPLC/MS retention time=4.0 min (Phenomenex Luna 5 micron C18 4.6 mm×50 mm column eluted with a 0% to 100% B solvent gradient over 4 min; solvent A=90% H$_2$O, 10% MeOH, 10 mM NH$_4$OAc and solvent B=10% H$_2$O, 90% MeOH, 10 mM NH$_4$OAc; flow rate=4.0 mL/min; UV detection at 220 nm); m/z=507 and 509 [M+H]$^+$, 505 and 507 [M−H]$^−$.

EXAMPLE 8

(S)—N-(1-Benzyl-6-bromo-2-oxo-1,2,3,4-tetrahydroquinolin-3-yl)-benzenesulfonamide

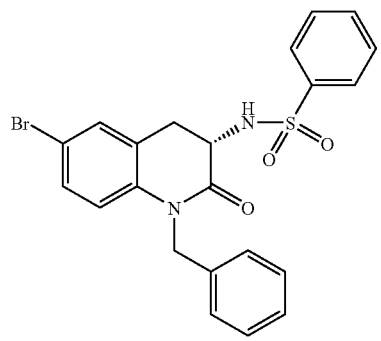

8A. (S)-(2-Oxo-1,2,3,4-tetrahydroquinolin-3-yl)-carbamic acid tert-butyl ester

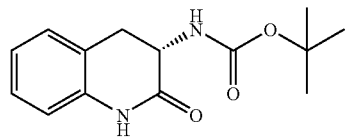

The title compound may be prepared either as described in US 2004/002495 or as follows: To a solution of (S)-2-(tert-butyloxycarbonylamino)-3-(2-nitrophenyl)propanoic acid (987 mg, 3.18 mmol, Peptech catalog # BL284) in MeOH (100 mL) was added 10% palladium on carbon (300 mg), and the mixture was stirred at RT under hydrogen at 80 psi for 24 h. Filtration and solvent evaporation under vacuum provided the title compound (800 mg) as a foam.

8B. (S)-(6-Bromo-2-oxo-1,2,3,4-tetrahydroquinolin-3-yl)-carbamic acid tert-butyl ester

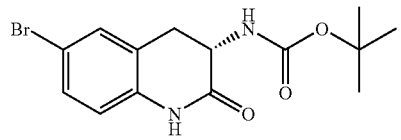

The title compound, which was isolated as a side-product of the preparation of 6A, may also be prepared from 8A as follows: To a solution of 8A (750 mg, 2.42 mmol) in MeOH (12 mL) and CH$_2$Cl$_2$ (12 mL) stirring at RT under argon was added CaCO$_3$ (484 mg, 4.83 mmol) and benzyltrimethylammonium tribromide (1885 mg, 4.83 mmol). After 18 h 10% aqueous NaHSO$_3$ (5 mL) was added to the reaction mixture, and stirring was continued for 30 min. Partial evaporation under vacuum was performed to remove nearly all of the organic solvents before the mixture was extracted twice with CH$_2$Cl$_2$. The combined extracts were washed with water, dried (MgSO$_4$), and evaporated under vacuum. The resulting residue was chromatographed on silica gel eluted with 25% Et$_2$O in CH$_2$Cl$_2$ to obtain the title compound (746 mg) as a white foam.

8C. (S)-(1-Benzyl-6-bromo-2-oxo-1,2,3,4-tetrahydroquinolin-3-yl)-carbamic acid tert-butyl ester

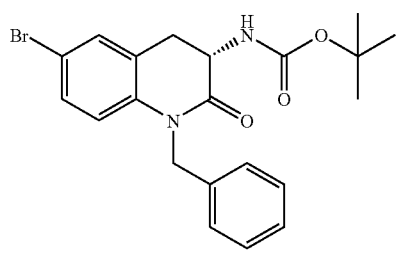

The title compound was prepared from 8B according to the procedures described in 3C.

8D. (S)-3-Amino-1-benzyl-6-bromo-2-oxo-1,2,3,4-tetrahydroquinoline, hydrochloric acid salt

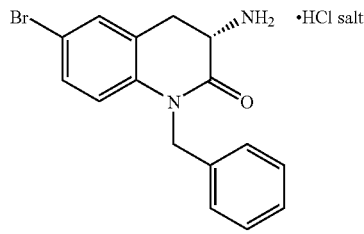

The title compound was prepared from 8C according to the procedures described in 3D.

8E. (S)—N-(1-Benzyl-6-bromo-2-oxo-1,2,3,4-tetrahydroquinolin-3-yl)-benzenesulfonamide The title compound was prepared from 8D according to the procedures described in 3E, except that in this case the title compound was purified by silica gel chromatography rather than preparative HPLC. The reaction mixture was loaded directly onto the column, which was eluted with 100% $CH_2Cl_2$. HPLC/MS retention time=3.8 min (Phenomenex Luna 5 micron C18 4.6 mm×50 mm column eluted with a 0% to 100% B solvent gradient over 4 min; solvent A=90% $H_2O$, 10% MeOH, 10 mM $NH_4OAc$ and solvent B=10% $H_2O$, 90% MeOH, 10 mM $NH_4OAc$; flow rate=4.0 mL/min; UV detection at 220 nm); m/z=471 and 473 $[M+H]^+$, 469 and 471 $[M-H]^-$.

EXAMPLE 9

(S)-N-(1-Benzyl-6-bromo-2-oxo-1,2,3,4-tetrahydroquinolin-3-yl)-3,5-difluorobenzenesulfonamide

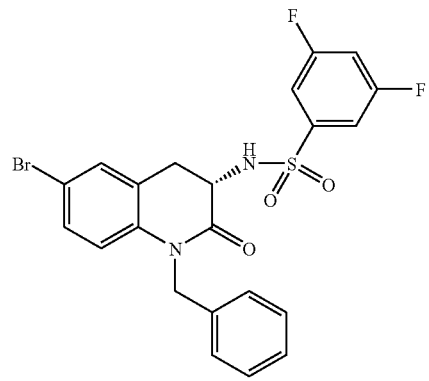

The title compound was prepared from 8D according to the procedures described in Example 7. HPLC/MS retention time=4.0 min (Phenomenex Luna 5 micron C18 4.6 mm×50 mm column eluted with a 0% to 100% B solvent gradient over 4 min; solvent A=90% $H_2O$, 10% MeOH, 10 mM $NH_4OAc$ and solvent B=10% $H_2O$, 90% MeOH, 10 mM $NH_4OAc$; flow rate=4.0 mL/min; UV detection at 220 nm); m/z=507 and 509 $[M+H]^+$, 505 and 507 $[M-H]^-$.

EXAMPLE 10

(S)-N-(1-Benzyl-6-cyano-2-oxo-1,2,3,4-tetrahydroquinolin-3-yl)-benzenesulfonamide A mixture of Example 8 (9 mg, 0.018 mmol), tetrakis (triphenylphosphine)-palladium (22 mg, 0.019 mmol), and $Zn(CN)_2$ (15 mg, 0.128 mmol) in DMF (1 mL) stirring under argon was heated to 120° for 1 h. After cooling to RT, the heterogeneous was diluted with a 80% MeOH in $H_2O$ solution and filtered. The filtrate was directly injected to reverse phase preparative HPLC, which provided the title compound (7 mg). HPLC/MS retention time=3.3 min (Phenomenex Luna 5 micron C18 4.6 mm×50 mm column eluted with a 0% to 100% B solvent gradient over 4 min; solvent A=90% $H_2O$, 10% MeOH, 10 mM $NH_4OAc$ and solvent B=10% $H_2O$, 90% MeOH, 10 mM $NH_4OAc$; flow rate=4.0 mL/min; UV detection at 220 nm); m/z=418 $[M+H]^+$, 416 $[M-H]^-$.

EXAMPLE 11

(S)-N-(1-Benzyl-6-cyano-2-oxo-1,2,3,4-tetrahydro-quinolin-3-yl)-3,5-difluorobenzenesulfonamide

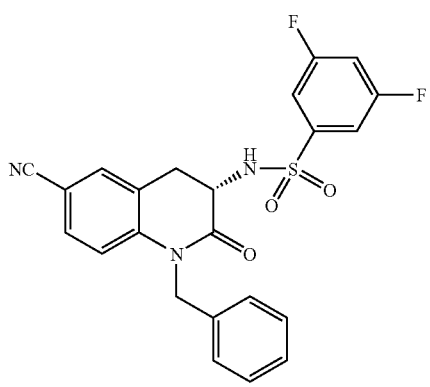

The title compound (50 mg) was prepared from Example 9 (60 mg) according to the procedures described in Example 10. HPLC/MS retention time=3.4 min (Phenomenex Luna 5 micron C18 4.6 mm×50 mm column eluted with a 0% to 100% B solvent gradient over 4 min; solvent A=90% $H_2O$, 10% MeOH, 10 mM $NH_4OAc$ and solvent B=10% $H_2O$, 90% MeOH, 10 mM $NH_4OAc$; flow rate=4.0 mL/min; UV detection at 220 nm); m/z=454 $[M+H]^+$, 452 $[M-H]^-$.

EXAMPLE 12

N-(1-Benzyl-2-oxo-6-(thiophen-3-yl)-1,2,3,4-tetrahydroquinolin-3-yl)-benzenesulfonamide

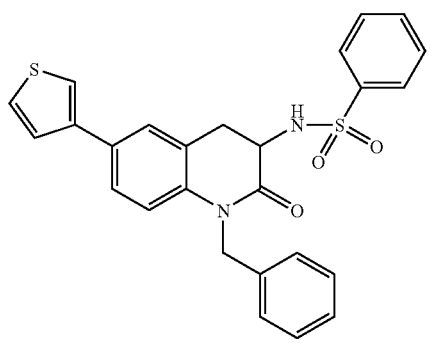

12A. (1-Benzyl-2-oxo-6-(thiophen-3-yl)-1,2,3,4-tetrahydroquinolin-3-yl)-carbamic acid tert-butyl ester

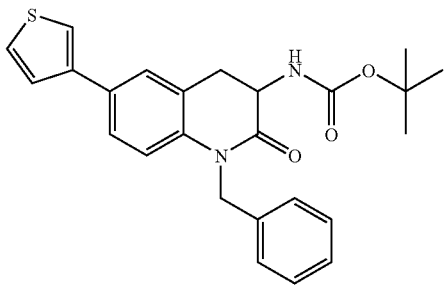

To a solution of 4A (25 mg, 0.043 mmol) in degassed THF (2 mL) was added tetrakis(triphenylphosphine)palladium (10 mg, 0.009 mmol), $K_2C_3$ (18 mg, 0.13 mmol), and 3-bromothiophene (21 mg, 0.13 mmol). The resulting mixture was heated at 70° for 16 h under argon. After cooling to RT, the mixture was filtered through Celite®, rinsing with $CH_2Cl_2$. The filtrate was evaporated under vacuum and the resulting residue was chromatographed on silica gel eluted with EtOAc in hexane to obtain the title compound (14.5 mg, somewhat impure).

12B. N-(1-Benzyl-2-oxo-6-(thiophen-3-yl)-1,2,3,4-tetrahydroquinolin-3-yl)-benzenesulfonamide The title compound (6 mg) was prepared from 12A (14.5 mg, somewhat impure) according to the procedures described in 3D and 3E. HPLC/MS retention time=3.9 min (Phenomenex Luna 5 micron C18 4.6 mm×50 mm column eluted with a 0% to 100% B solvent gradient over 4 min; solvent A=90% $H_2O$, 10% MeOH, 10 mM $NH_4OAc$ and solvent B=10% $H_2O$, 90% MeOH, 10 mM $NH_4OAc$; flow rate=4.0 mL/min; UV detection at 220 nm); m/z=475 $[M+H]^+$.

BIOLOGICAL EVALUATION

Cannabinoid Receptor Binding Assay

Radioligand binding studies were conducted in membranes prepared from Chinese Hamster Ovary (CHO) cells that over-express recombinant human CB-1 (CHO-CB-1 cells). Total assay volume for the binding studies was 100 µl. 5 ug of membranes were brought up to a final volume of 95 µl with Binding Buffer (25 mM HEPES, 150 mM NaCl, 2.5 mM $CaCl_2$, 1 mM $MgCl_2$, 0.25% BSA). The diluted membranes were preincubated with a compound or DMSO vehicle. The binding reaction was initiated by the addition of 2 nM final $^3$H-CP-55,940 (120 Ci/mmol) and proceeded for 2.5 hours at room temperature. The binding reaction was terminated by transferring the reaction to GF/B 96 well plates (presoaked with 0.3% polyethylenimine) using a Packard Cell Harvester. The filter was washed with 0.25× PBS, 30 µl MicroScint was added per well, and the bound radiolabel was quantitated by scintillation counting on a Packard TopCount Scintillation Counter. The CB-2 radioligand binding assay was conducted identically except that the membranes from CHO-CB-2 cells were used.

For a compound to be considered a CB-1 antagonist, the compound must possess a CB-1 receptor binding affinity Ki less than 4000 nM. As determined by the assay described above, the CB-1 receptor binding $K_i$ values of working Examples 1-12 fall within the range of 0.01 nM to 4000 nM.

Cannabinoid Receptor Functional Activity Assay

Functional CB-1 inverse agonist activity of test compounds was determined in CHO-CB-1 cells using a cAMP accumulation assay. CHO-CB-1 cells were grown in 96 well plates to near confluence. On the day of the functional assay, growth medium was aspirated and 100 of Assay Buffer (PBS plus 25 mM HEPES/0.1 mM 3isobutyl-1-methylxanthine/ 0.1% BSA) was added. Compounds were added to the Assay buffer diluted 1:100 from 100% DMSO and allowed to preincubate for 10 minutes prior to addition of 5 uM forskolin. The mixture was allowed to proceed for 15 minutes at room temperature and was terminated by the addition of 0.1 N HCl. The total intracellular cAMP concentration was quantitated using the Amersham cAMP SPA kit.

UTILITIES & COMBINATIONS

A. Utilities

The compounds of the present invention are cannabinoid receptor modulators, and include compounds which are, for example, selective agonists, partial agonists, inverse agonists, antagonists or partial antagonists of the cannabinoid receptor. Accordingly, the compounds of the present invention may be useful for the treatment or prevention of diseases and disorders associated with G-protein coupled cannabinoid receptor activity. Preferably, compounds of the present invention possess activity as antagonists or inverse agonists of the CB-1 receptor, and may be used in the treatment of diseases or disorders associated with the activity of the CB-1 receptor.

Accordingly, the compounds of the present invention can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, hypertension, insulin resistance, hypercholesterolemia, hypertriglyceridemia, cholelithiasis and sleep disorders, hyperlipidemic conditions, bulimia nervosa and compulsive eating disorders) or psychiatric disorders, such as substance abuse, depression, anxiety, mania and schizophrenia. These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxin-induced hypotension). These compounds could also be used for treatment of catabolism in connection with pulmonary dysfunction and ventilator dependency; treatment of cardiac dysfunction (e.g., associated with valvular disease, myocardial infarction, cardiac hypertrophy or congestive heart failure); and improvement of the overall pulmonary function; transplant rejection; rheumatoid arthritis; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury.

Compounds useful in the treatment of appetitive or motivational disorders regulate desires to consume sugars, carbohydrates, alcohol or drugs and more generally to regulate the consumption of ingredients with hedonic value. In the present description and in the claims, appetitive disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present invention therefore further relates to the use of a CB-1 receptor antagonist or inverse agonist for the treatment of bulimia and obesity, including obesity associated with type II diabetes (non-insulin-dependent diabetes), or more generally any disease resulting in the patient becoming overweight. Obesity, as described herein, is defined by a body mass index ($kg/m^2$) of at least 26. It may be due to any cause, whether genetic or environmental, including overeating and bulemia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present invention may also be useful in treating substance abuse disorders, including substance dependence or abuse without physiological dependence. Substances of abuse include alcohol, amphetamines (or amphetamine-like substances), caffeine, cannabis, cocaine, hallucinogens, inhalents, nicotine, opioids, phencyclidine (or phencyclidine-like compounds), sedative-hypnotics or benzodiazepines, and other (or unknown) substances and combinations of the above. The terms "substance abuse disorders" also includes drug or alcohol withdrawal syndromes and substance-induced anxiety or mood disorder with onset during withdrawal.

Compounds in the present invention may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. Dementias are diseases that include memory loss and additional intellectual impairment separate from memory. Cannabinoid receptor modulators may also be useful in treating cognitive impairments related to attentional deficits, such as attention deficit disorder.

Compounds in the present invention may also be useful in treating diseases associated with dysfunction of brain dopaminergic systems, such as Parkinson's Disease and substance abuse disorders. Parkinsons's Disease is a neurodenerative movement disorder characterized by bradykinesia and tremor.

As modulators of the cannabinoid receptor, the compounds of the present invention are further useful for the treatment and prevention of respiratory diseases and disorders. Respiratory diseases for which cannabinoid receptor modulators are useful include, but are not limited to, chronic pulmonary obstructive disorder, emphysema, asthma, and bronchitis. In addition, cannabinoid receptor modulators block the activation of lung epithelial cells by moeties such as allergic agents, inflammatory cytokines or smoke, thereby limiting release of mucin, cytokines, and chemokines, or selectively inhibiting lung epithelial cell activation.

Moreover, the compounds employed in the present invention may stimulate inhibitory pathways in cells, particularly in leukocytes, lung epithelial cells, or both, and are thus useful in treating such diseases. "Leukocyte activation" is defined herein as any or all of cell proliferation, cytokine production, adhesion protein expression, and production of inflammatory mediators. "Epithelial cell activation" is defined herein as the production of any or all of mucins, cytokines, chemokines, and adhesion protein expression.

Use of the compounds of the present invention for treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia greata; chronic actinic dermatitis; eczema; Behcet's disease; Pustulosis palmoplanteris; Pyoderma gangrenum; Sezary's syndrome; atopic dermatitis; systemic schlerosis; and morphea. The term "leukocyte activation-associated" or "leukocyte-activation mediated" disease as used herein includes each of the above referenced diseases or disorders. In a particular embodiment, the compounds of the present invention are useful for treating the aforementioned exemplary disorders irrespective of their etiology. The combined activity of the present compounds towards monocytes, macrophages, T-cells, etc. may be useful in treating any of the above-mentioned disorders.

Cannabinoid receptors are important in the regulation of Fc gamma receptor responses of monocytes and macrophages. Compounds of the present invention inhibit the Fc gamma dependent production of TNF alpha in human monocytes/macrophages. The ability to inhibit Fc gamma receptor dependent monocyte and macrophage responses results in additional anti-inflammatory activity for the present compounds. This activity is especially of value, for example, in treating inflammatory diseases such as arthritis or inflammatory bowel disease. In particular, the present compounds are useful for treating autoimmune glomerulonephritis and other instances of glomerulonephritis induced by deposition of immune complexes in the kidney that trigger Fc gamma receptor responses leading to kidney damage.

Cannabinoid receptors are expressed on lung epithelial cells. These cells are responsible for the secretion of mucins and inflammatory cytokines/chemokines in the lung and are thus intricately involved in the generation and progression of respiratory diseases. Cannabinoid receptor modulators regulate both the spontaneous and the stimulated production of both mucins and cytokines. Thus, such compounds are useful in treating respiratory and pulmonary diseases including, COPD, ARDS, and bronchitis.

Further, cannabinoid receptors may be expressed on gut epithelial cells and hence regulate cytokine and mucin production and may be of clinical use in treating inflammatory diseases related to the gut. Cannabinoid receptors are also expressed on lymphocytes, a subset of leukocytes. Thus, cannabinoid receptor modulators will inhibit B and T-cell activation, proliferation and differentiation. Thus, such compounds will be useful in treating autoimmune diseases that involve either antibody or cell mediated responses such as multiple sclerosis and lupus.

In addition, cannabinoid receptors regulate the Fc epsilon receptor and chemokine induced degranulation of mast cells and basophils. These play important roles in asthma, allergic rhinitis, and other allergic disease. Fc epsilon receptors are stimulated by IgE-antigen complexes. Compounds of the present invention inhibit the Fc epsilon induced degranulation responses, including the basophil cell line, RBL. The ability to inhibit Fc epsilon receptor dependent mast cell and basophil responses results in additional anti-inflammatory and anti-allergic activity for the present compounds. In particular, the present compounds are useful for treating asthma, allergic rhinitis, and other instances of allergic disease.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the cannabinoid receptor modulators in accordance with the invention.

Examples of suitable anti-obesity agents for use in combination with the compounds of the present invention include melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inihibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR α antagonists or agonists, PPAR α/γ dual agonists, 11-β-HSD-1 inhibitors, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR Y agonist such as a thiazolidinedione oral anti-diabetic agent or other insulin sensitizers (which have an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in, K. Yajima, et. al., Am. J. Physiol. Endocrinol. Metab., 284: E966-E971 (2003)), AZ-242 (tesaglitazar; Astra-Zeneca; as described in B. Ljung, et. al., J. Lipid Res., 43, 1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller, et al, J. Med. Chem., 31, 1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano, et al, J. Med. Chem., 20, 243-249 (1977), the farnesyl diphosphate analog A and presqualene pyrophosphate (PSQ-PP) analogs as disclosed by Corey and Volante, *J. Am. Chem. Soc.*, 98, 1291-1293 (1976), phosphinylphosphonates reported by McClard, R. W. et al., *J. Am. Chem. Soc.*, 109, 5544 (1987) and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SEC-HOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phoryl-choline (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future*, 24, 9-15 (1999), (Avasimibe); "The ACAT inhibitor, Cl-1011 is effective in the prevention and regression of aortic fatty streak area in hamsters", Nicolosi et al, *Atherosclerosis* (Shannon, Irel), 137 (1), 77-85 (1998); "The pharmacological profile of FCE 27677: a novel ACAT inhibitor with potent hypolipidemic activity mediated by selective suppression of the hepatic secretion of ApoB 100-containing lipoprotein", Ghiselli, Giancarlo, *Cardiovasc. Drug Rev.*, 16 (1), 16-30 (1998); "RP 73163: a bioavailable alkylsulfinyl-diphenylimidazole ACAT inhibitor", Smith, C., et al, *Bioorg. Med. Chem. Lett*, 6 (1), 47-50 (1996); "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., *Inflammation: Mediators Pathways*, 173-98 (1995), Publisher: CRC, Boca Raton, Fla.; "ACAT inhibitors: potential anti-atherosclerotic agents", Sliskovic et al, Curr. Med. Chem., 1 (3), 204-25 (1994); "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", Stout et al, *Chemtracts: Org. Chem.*, 8 (6), 359-62 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis* 115, 45-63 (1995) and *J. Med. Chem.* 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in Drugs of the Future, 24, 425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015,201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B 12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050,574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Cannbinoid receptor modulators could be useful in treating other diseases associated with obesity, including sleep disorders. Therefore, the compounds described in the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

Cannabinoid receptor modulators may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSR1), methadone, buprenorphine, nicotine and bupropion.

Cannabinoid receptor modulators may reduce anxiety or depression; therefore, the compounds described in this application may be used in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpah-adrenoreceptor antagonists, and atypical antidepressants (bupropion, lithium, nefazodone, trazodone and viloxazine).

The combination of a conventional antipsychotic drug with a CB-1 receptor antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), dipheyylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, shcizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and nootropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transportor modulators, such as ropinirole, or pramipexole or neurotrophic factors such as glial derived neurotrophic factor (GDNF).

The compounds described in the present invention could be used in combination with suitable anti-inflammatory agents. Examples of suitable anti-inflammatory agents for use in combination with the compounds of the present invention include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®, CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384, including TNF-alpha inhibitors, such as tenidap, anti-TNF antibodies or soluble TNF receptor such as etanercept (Enbrel®), rapamycin (sirolimus or Rapamune) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelnorm® and Maxi-K® openers such as those disclosed in U.S. Pat. No. 6,184,231 B1).

Exemplary of such other therapeutic agents which may be used in combination with cannabinoid receptor modulators include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: Hollenbaugh, D., Et Al, "Cleavable CD40Ig Fusion Proteins and the Binding to Sgp39", *J. Immunol. Methods* (Netherlands), 188 (1), pp. 1-7 (Dec. 15, 1995); Hollenbaugh, D., et al, "The Human T Cell Antigen Gp39, A Member of the TNF Gene Family, Is a Ligand for the CD40 Receptor: Expression of a Soluble Form of Gp39 with B Cell Co-Stimulatory Activity", *EMBO J.* (England), 11 (12), pp. 4313-4321 (December 1992); and Moreland, L. W. et al., "Treatment of Rheumatoid Arthritis with a Recombinant Human Tumor Necrosis Factor Receptor (P75)-Fc Fusion Protein," *New England J. of Medicine,* 337 (3), pp. 141-147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of formula I of the invention can be administered orally or parenterally, such as subcutaneously or intravenously, as well as by nasal application, rectally or sublingually to various mammalian species known to be subject to such maladies, e.g., humans, in an effective amount up to 1 gram, preferably up to 200 mg, more preferably to 50 mg in a regimen of single, two or four divided daily doses.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A compound of formula I

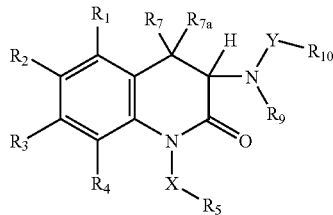

including all pharmaceutically acceptable salts and stereoisomers,
wherein:

$R_1$, $R_3$ and $R_4$ are each independently selected from the group consisting of hydrogen, alkyl, halo and CN;

$R_2$ is selected from the group consisting of alkenyl, alkynyl, cycloalkyl, cycloalkylalkyl, heterocyclyl, heterocycloalkyl, heteroaryl, arylalkyl, heteroarylalkyl, acyl, $OR_{11}$ and $OCF_2H$;

$R_5$ is selected from the group consisting of alkyl, alkenyl, alkynyl, cycloalkyl, heterocyclyl, aryl, heteroaryl, $COOR_{13}$ and $CONR_{13}R_{13a}$;

$R_7$ and $R_{7a}$ are each independently selected from the group consisting of hydrogen, alkyl and cycloalkyl;

$R_9$ is selected from the group consisting of hydrogen, alkyl, alkenyl, alkynyl, cycloalkyl, cycloalkylalkyl, heterocyclyl, heterocycloalkyl, arylalkyl and heteroarylalkyl;

$R_{10}$ is selected from the group consisting of alkenyl, alkynyl, cycloalkyl, cycloalkylalkyl, heterocyclyl, heterocycloalkyl, aryl, heteroaryl, arylalkyl and heteroarylalkyl;

$R_{11}$ is selected from the group consisting of aryl, heteroaryl and heteroarylalkyl;

$R_{13}$ and $R_{13a}$ are each independently selected from the group consisting of hydrogen, alkyl, alkenyl, alkynyl, cycloalkyl, cycloalkylalkyl, heterocyclyl, heterocycloalkyl, aryl, heteroaryl, arylalkyl and heteroarylalkyl;

or $R_{13}$ and $R_{13a}$ taken together can form cycloalkyl or heterocyclyl;

X is $—(CR_{14}R_{14a})_n—$;

Y is independently selected from the group consisting of $—S(O)_2—$ and $—SO_2N(R_{15})—$;

$R_{14}$ and $R_{14a}$ are each independently selected from the group consisting of hydrogen and alkyl;

$R_{15}$ is selected from the group consisting of hydrogen, alkyl, alkenyl, alkynyl, cycloalkyl, cycloalkylalkyl, heterocyclyl, heterocycloalkyl, aryl, heteroaryl, arylalkyl and heteroarylalkyl;

or $R_{10}$ and $R_{15}$ taken together can form cycloalkyl or heterocyclyl; and n is an integer 0, 1 or 2, with the following provisos
$R_5$ is neither imidazole nor substituted imidazole;
when Y is $—S(O)_2—$, $R_{10}$ is not a seven-membered lactam; and
when Y is $—SO_2N(R_{15})—$, neither $R_{10}$ nor $R_{15}$ is a seven-membered lactam.

2. The compound of claim 1, including all pharmaceutically acceptable salts and stereoisomers, wherein:

$R_2$ is selected from the group consisting of heteroaryl, arylalkyl, $OR_{11}$ and $OCF_2H$;

$R_5$ is selected from the group consisting of aryl and heteroaryl;

$R_9$ is hydrogen;

$R_{10}$ is selected from the group consisting of aryl, heteroaryl, arylalkyl and heteroarylalkyl; and X is $CH_2$.

3. The compound of claim 2, including all pharmaceutically acceptable salts and stereoisomers, wherein:

$R_1$, $R_3$ and $R_4$ are each hydrogen;

$R_5$ is aryl;

$R_7$ and $R_{7a}$ are each hydrogen; and

Y is $—S(O)_2—$.

4. The compound of claim 1, including all pharmaceutically acceptable salts and stereoisomers, selected from the group consisting of:

N-(1,6-Dibenzyl-2-oxo-1,2,3,4-tetrahydroquinolin-3-yl)-benzenesulfonamide and

N-(1-Benzyl-2-oxo-6-(thiophen-3-yl)-1,2,3,4-tetrahydroquinolin-3-yl)-benzenesulfonamide.

* * * * *